(12) United States Patent
Kino et al.

(10) Patent No.: US 9,081,199 B2
(45) Date of Patent: Jul. 14, 2015

(54) PROCESS FOR THE PRODUCTION OF DIPEPTIDES BY A DIPEPTIDE-SYNTHESIZING ENZYME

(75) Inventors: Kuniki Kino, Chiba (JP); Yuji Nakazawa, Tokorozawa (JP); Makoto Yagasaki, Hofu (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 1098 days.

(21) Appl. No.: 11/817,905

(22) PCT Filed: Mar. 17, 2006

(86) PCT No.: PCT/JP2006/305343
§ 371 (c)(1),
(2), (4) Date: Sep. 6, 2007

(87) PCT Pub. No.: WO2006/101023
PCT Pub. Date: Sep. 28, 2006

(65) Prior Publication Data
US 2009/0047706 A1    Feb. 19, 2009

(30) Foreign Application Priority Data
Mar. 18, 2005 (JP) ................. 2005-079986

(51) Int. Cl.
C12P 21/00 (2006.01)
G02B 21/26 (2006.01)
C12N 9/00 (2006.01)
G02B 21/36 (2006.01)

(52) U.S. Cl.
CPC *G02B 21/26* (2013.01); *C12N 9/93* (2013.01); *G02B 21/362* (2013.01)

(58) Field of Classification Search
CPC ........... C12P 21/00; C12P 21/02; C12N 9/93; C07K 5/00; C07K 5/04; C07K 5/06; C12Y 603/02028
USPC ............ 435/68.1, 71.1, 183, 325, 419, 252.3, 435/254.11, 257.2
See application file for complete search history.

(56) References Cited

U.S. PATENT DOCUMENTS

| | | | | |
|---|---|---|---|---|
| 4,335,209 | A * | 6/1982 | Asai et al. ...................... | 435/108 |
| 5,652,116 | A | 7/1997 | Grandi et al. | |
| 5,795,738 | A | 8/1998 | Grandi et al. | |
| 7,514,242 | B2 * | 4/2009 | Hashimoto et al. ........... | 435/128 |
| 7,514,243 | B2 * | 4/2009 | Hashimoto et al. ........... | 435/128 |
| 2004/0171106 | A1 | 9/2004 | Hashimoto et al. | |

FOREIGN PATENT DOCUMENTS

| | | |
|---|---|---|
| JP | 58-146539 | 9/1983 |
| JP | 58-209991 | 12/1983 |
| JP | 58-209992 | 12/1983 |
| JP | 59-106298 | 6/1984 |

OTHER PUBLICATIONS

TrEMBL accession No. Q8XQ00 (Nov. 2009), 4 pages.*
Galperin et al., "A diverse superfamily of enzymes with ATP-dependent carboxylate-amine/thiol ligase activity", Protein Sci. 6:2639-2643, 1997.*
GenBank Accession No. Q8XQ00, Mar. 2004; filed by applicant on Mar. 5, 2010.*
Park et al., J. Biol. Chem. 272:9210-9214, 1997.*
Zawadzke et al., Biochemistry 30:1673-1682, 1991.*
Sato et al., J. Biosci. Bioengineer. 99:623-628, Jun. 2005.*
Kino et al., "Dipeptide synthesis by L-amino acid ligase from *Ralstonia solanacearum*", Biochem. Biophys. Res. Comm. 371:536-540, 2008.*
Roise et al., "Inactivation of the *Pseudomonas striata* Broad Specificity Amino Acid Racemase by D and L Isomers of B-Substituted Alanines: Kinetics, Stoichiometry, Active Site Peptide, and Mechanistic Studies", Biochemistry 23:5195-5201, 1984.*
Kenzo Yokozeki et al., "A Novel and Efficient enzymatic method for the production of peptides from unprotected starting materials," Journal of Biotechnology, 115 (2005) 211-220.
Sakajoh, et al., "Cell-free synthesis of the dipeptide antibiotic bacilysin", Journal of Industrial Microbiology, vol. 2 (1987) 201-8.
Bergmann, et al., "The role of specificity in the enzymatic synthesis of proteins", Journal of Biological Chemistry, vol. 119 (1937) 707-20.
Doekel, et al., "Dipeptide formation on engineered hybrid peptide synthetases", Chemistry & Biology, vol. 7, No. 6 (2000) 373-84.
Dieckmann, et al., "Dipeptide synthesis by an isolated adenylate-forming domain of non-ribosomal peptide synthetases (NRPS)", FEBS Letters, vol. 498 (2001) 42-5.
Yazgan, et al., "Bacilysin biosynthesis by a partially-purified enzyme fraction from *Bacillus subtilis*", Enzyme and Microbial Technology, vol. 29 (2001) 400-6.
Salanoubat, et al., "Genone sequence of the plant pathogen *Ralstonia solanacearum*", Nature, vol. 415, No. 6871 (2002) 497-502.
Sato, et al., Koso Kagaku Kenkyukai Dai 52 kai Koenkai Koen Yoshishu, No. 52 (2004) 44 (with translation).
Tabata, et al., "Shinki Dipeptide Gose Koso no Cloning to Seishitsu Kaiseki", Nippon Nogei Kagakukai Taikai Koen Yoshish (2005) p. 36, 29D081a (with translation).

* cited by examiner

*Primary Examiner* — David J Steadman
(74) *Attorney, Agent, or Firm* — Fitzpatrick, Cella, Harper & Scinto

(57) ABSTRACT

The present invention provides: a protein having dipeptide-synthesizing activity; DNA encoding the protein; a recombinant DNA comprising the DNA; a transformant transformed with the recombinant DNA; a process for producing the protein having dipeptide-synthesizing activity using the transformant or the like; a process for producing a dipeptide using the protein having dipeptide-synthesizing activity; and a process for producing a dipeptide using, as an enzyme source, a culture of a transformant or a microorganism which produces the protein having dipeptide-synthesizing activity or the like.

6 Claims, 1 Drawing Sheet

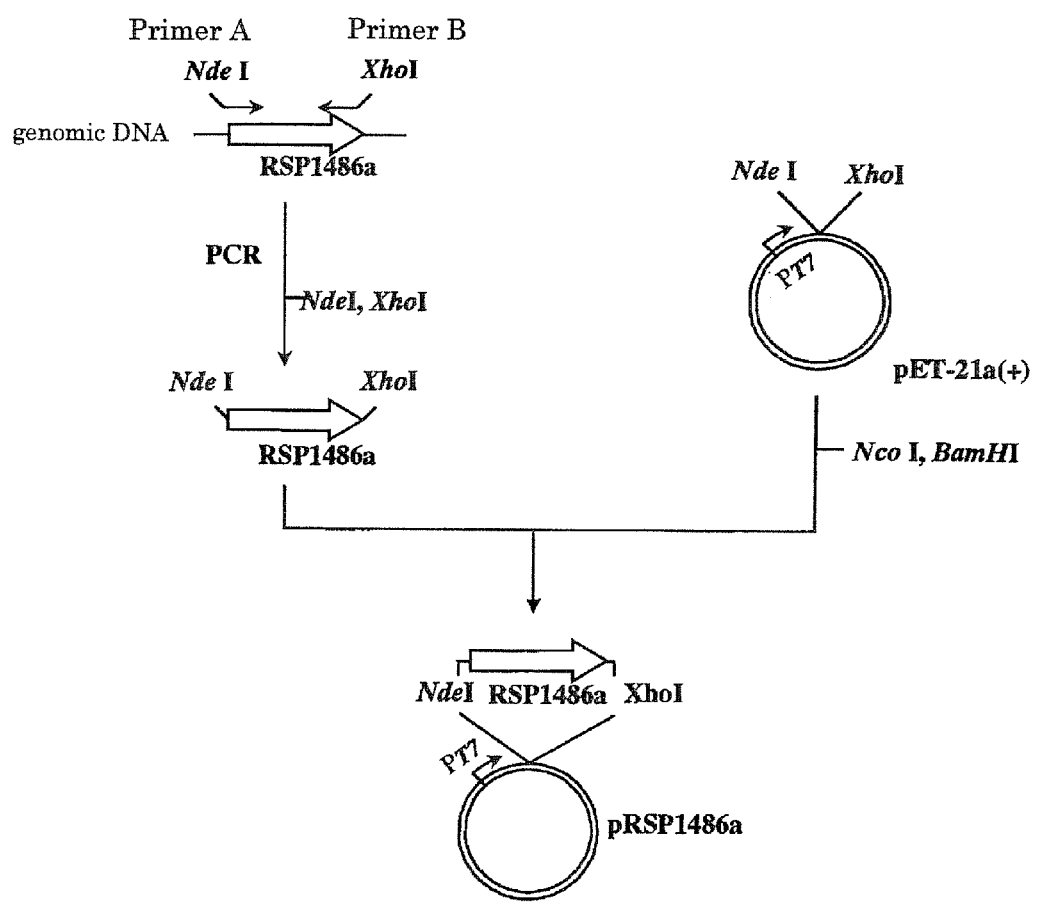

PROCESS FOR THE PRODUCTION OF DIPEPTIDES BY A DIPEPTIDE-SYNTHESIZING ENZYME

TECHNICAL FIELD

The present invention relates to a protein having dipeptide-synthesizing activity, DNA encoding the protein, a recombinant DNA comprising the DNA, a transformant transformed with the recombinant DNA, a process for producing the protein having dipeptide-synthesizing activity, a process for producing a dipeptide using the protein having dipeptide-synthesizing activity, and a process for producing a dipeptide using a microorganism or a transformant which produces the protein having dipeptide-synthesizing activity.

BACKGROUND ART

As for the method for large-scale peptide synthesis, chemical synthesis methods (liquid phase method and solid phase method), enzymatic synthesis methods and biological synthesis methods utilizing recombinant DNA techniques are known. Currently, the enzymatic synthesis methods and biological synthesis methods are employed for the synthesis of long-chain peptides longer than 50 residues, and the chemical synthesis methods and enzymatic synthesis methods are mainly employed for the synthesis of dipeptides.

In the synthesis of dipeptides by the chemical synthesis methods, operations such as introduction and removal of protective groups for functional groups are necessary, and racemates are also formed. The chemical synthesis methods are thus considered to be disadvantageous in respect of cost and efficiency. They are unfavorable also from the viewpoint of environmental hygiene because of the use of large amounts of organic solvents and the like.

As to the synthesis of dipeptides by the enzymatic methods, the following methods are known: a method utilizing reverse reaction of protease (see non-patent publication No. 1); methods utilizing thermostable aminoacyl t-RNA synthetase (see patent publication Nos. 1 to 4); and methods utilizing non-ribosomal peptide synthetase (hereinafter referred to as NRPS) (see non-patent publication Nos. 2 and 3 and patent publication Nos. 5 and 6).

However, the method utilizing reverse reaction of protease requires introduction and removal of protective groups for functional groups of amino acids used as substrates, which causes difficulties in raising the efficiency of peptide-forming reaction and in preventing peptidolytic reaction. The methods utilizing thermostable aminoacyl t-RNA synthetase have the defects that the expression of the enzyme and the prevention of side reactions forming by-products other than the desired products are difficult. The methods utilizing NRPS are inefficient in that the expression of the enzyme by recombinant DNA techniques is difficult because the enzyme molecule is huge, and in that the supply of coenzyme 4'-phosphopantetheine is necessary.

On the other hand, there exist a group of peptide synthetases that have enzyme molecular weight lower than that of NRPS and do not require coenzyme 4'-phosphopantetheine; for example, γ-glutamylcysteine synthetase, glutathione synthetase, D-alanine-D-alanine (D-Ala-D-Ala) ligase, and poly-γ-glutamate synthetase. Most of these enzymes utilize D-amino acids as substrates or catalyze peptide bond formation at the γ-carboxyl group. Because of such properties, they can not be used for the synthesis of dipeptides by peptide bond formation at the α-carboxyl group of L-amino acid.

The only known example of an enzyme capable of forming a dipeptide by the activity to form a peptide bond at the α-carboxyl group of L-amino acid is bacilysin (dipeptide antibiotic derived from a microorganism belonging to the genus *Bacillus*) synthetase. Bacilysin synthetase is known to have the activity to synthesize bacilysin [L-alanyl-L-anticapsin (L-Ala-L-anticapsin)] and L-alanyl-L-alanine (L-Ala-L-Ala) (see non-patent publication Nos. 4 and 5). Recently, it has been reported that this enzyme has the activity to form various kinds of dipeptides from various combinations of the same or different free amino acids (see patent publication No. 7).

However, there exists a need for a novel dipeptide-synthesizing enzyme which has substrate specificity different from that of the above enzyme, because the above enzyme can not form all dipeptides efficiently due to its substrate specificity.

The nucleotide sequence of the chromosomal DNA and the presumed nucleotide sequences of genes of *Ralstonia solanacearum* GMI1000 are both known. However, neither the function of a protein encoded by RSP1486 gene nor whether RSP1486 gene actually encodes a protein having a function is not known.

Patent publication No. 1:
  Japanese Published Unexamined Patent Application No. 146539/83
Patent publication No. 2:
  Japanese Published Unexamined Patent Application No. 209991/83
Patent publication No. 3:
  Japanese Published Unexamined Patent Application No. 209992/83
Patent publication No. 4:
  Japanese Published Unexamined Patent Application No. 106298/84
Patent publication No. 5:
  U.S. Pat. No. 5,795,738
Patent publication No. 6:
  U.S. Pat. No. 5,652,116
Patent publication No. 7:
  WO04/058960 pamphlet
Non-patent publication No. 1:
  J. Biol. Chem., 119, 707-720 (1937)
Non-patent publication No. 2:
  Chem. Biol., 7, 373-384 (2000)
Non-patent publication No. 3:
  FEBS Lett., 498, 42-45 (2001)
Non-patent publication No. 4:
  J. Ind. Microbiol., 2, 201-208 (1987)
Non-patent publication No. 5:
  Enzyme. Microbial. Technol., 29, 400-406 (2001)

DISCLOSURE OF THE INVENTION

Problems to be Solved by the Invention

An object of the present invention is to provide: a protein having dipeptide-synthesizing activity; DNA encoding the protein; a recombinant DNA comprising the DNA; a transformant transformed with the recombinant DNA; a process for producing the protein having dipeptide-synthesizing activity using the transformant or the like; a process for producing a dipeptide using the protein having dipeptide-synthesizing activity; and a process for producing a dipeptide using, as an enzyme source, a culture of a transformant or a microorganism which produces the protein having dipeptide-synthesizing activity or the like.

Means for Solving the Problems

The present invention relates to the following (1) to (10).

(1) A protein according to any of the following [1] to [3]:
  [1] a protein having the amino acid sequence shown in any of SEQ ID NOS: 1 to 9;
  [2] a protein consisting of an amino acid sequence wherein one or more amino acid residues are deleted, substituted or added in the amino acid sequence shown in any of SEQ ID NOS: 1 to 9 and having dipeptide-synthesizing activity; and
  [3] a protein consisting of an amino acid sequence which has 80% or more homology to the amino acid sequence shown in any of SEQ ID NOS: 1 to 9 and having dipeptide-synthesizing activity.
(2) A DNA according to any of the following [1] to [3]:
  [1] DNA encoding the protein according to the above (1);
  [2] DNA having the nucleotide sequence shown in any of SEQ ID NOS: 10 to 21; and
  [3] DNA which hybridizes with DNA having a nucleotide sequence complementary to the nucleotide sequence shown in any of SEQ ID NOS: 10 to 21 under stringent conditions and which encodes a protein having dipeptide-synthesizing activity.
(3) A recombinant DNA comprising the DNA according to the above (2).
(4) A transformant carrying the recombinant DNA according to the above (3).
(5) The transformant according to the above (4), wherein the transformant is a transformant obtained by using a microorganism as a host.
(6) The transformant according to the above (5), wherein the microorganism is a microorganism belonging to the genus *Escherichia*.
(7) A process for producing the protein according to the above (1), which comprises culturing a microorganism having the ability to produce the protein according to the above (1) in a medium, allowing the protein to form and accumulate in the culture, and recovering the protein from the culture.
(8) The process according to the above (7), wherein the microorganism having the ability to produce the protein according to the above (1) is the transformant according to any one of the above (4) to (6).
(9) A process for producing a dipeptide which comprises allowing a culture of a microorganism having the ability to produce the protein according to the above (1) or a treated matter of the culture, or the protein according to the above (1), and one or more kinds of amino acids to be present in an aqueous medium, allowing the dipeptide to form and accumulate in the medium, and recovering the dipeptide from the medium.
(10) The process according to the above (9), wherein the microorganism having the ability to produce the protein according to the above (1) is the transformant according to any one of the above (4) to (6).

EFFECT OF THE INVENTION

In accordance with the present invention, a protein having the activity to synthesize a dipeptide can be produced, and a dipeptide can be produced by using the protein, or a transformant or a microorganism which has the ability to produce the protein.

BRIEF DESCRIPTION OF THE DRAWINGS

FIG. 1 shows the steps for constructing plasmid pRSP1486a.

EXPLANATION OF SYMBOLS

In FIG. 1, RSP1486a represents RSP1486a gene derived from *Ralstonia solanacearum* ATCC 11696, and PT7 represents T7 promoter gene.

BEST MODES FOR CARRYING OUT THE INVENTION

1. Proteins of the Present Invention

The proteins of the present invention include:
[1] a protein having the amino acid sequence shown in any of SEQ ID NOS: 1 to 9;
[2] a protein consisting of an amino acid sequence wherein one or more amino acid residues are deleted, substituted or added in the amino acid sequence shown in any of SEQ ID NOS: 1 to 9 and having dipeptide-synthesizing activity; and
[3] a protein consisting of an amino acid sequence which has 80% or more homology to the amino acid sequence shown in any of SEQ ID NOS: 1 to 9 and having dipeptide-synthesizing activity.

The above protein consisting of an amino acid sequence wherein one or more amino acid residues are deleted, substituted or added and having dipeptide-synthesizing activity can be obtained, for example, by introducing a site-directed mutation into DNA encoding a protein consisting of the amino acid sequence shown in any of SEQ ID NOS: 1 to 9 by site-directed mutagenesis described in Molecular Cloning, A Laboratory Manual, Second Edition, Cold Spring Harbor Laboratory Press (1989) (hereinafter referred to as Molecular Cloning, Second Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above site-directed mutagenesis. The suitable number is 1 to dozens, preferably 1 to 20, more preferably 1 to 10, further preferably 1 to 5.

The expression "one or more amino acid residues are deleted, substituted or added in the amino acid sequence shown in any of SEQ ID NOS: 1 to 9" means that the amino acid sequence may contain deletion, substitution or addition of a single or plural amino acid residues at an arbitrary position therein.

Amino acid residues that may be substituted are, for example, those which differ between any two amino acid sequences when the amino acid sequences shown in SEQ ID NOS: 1 to 9 are compared using known alignment software. An example of known alignment software is alignment analysis software contained in gene analysis software Genetyx (Software Development Co., Ltd.). As analysis parameters for the analysis software, default values can be used.

Deletion or addition of amino acid residues may be contained, for example, in the N-terminal or C-terminal one to several amino acid region of the amino acid sequence shown in any of SEQ ID NOS: 1 to 9.

Deletion, substitution and addition may be simultaneously contained in one sequence, and amino acids to be substituted or added may be either natural or not. Examples of the natural amino acids are L-arginine, L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine In order that the protein of the present invention may have dipeptide-synthesizing activity, it is desirable that the homology of its amino acid sequence to the amino acid sequence shown in any of SEQ ID NOS: 1 to 9, preferably the amino acid sequence shown in SEQ ID NO: 1 is 80% or more, preferably 90% or more, more preferably 94% or more, further preferably 98% or more, and particularly preferably 99% or more.

The homology among amino acid sequences and nucleotide sequences can be determined by using algorithm BLAST by Karlin and Altschul [Pro. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known.

A protein consisting of an amino acid sequence which has 80% or more homology, preferably 90% or more homology, more preferably 94% or more homology, further preferably 98% or more homology, particularly preferably 99% or more homology to the amino acid sequence shown in any of SEQ ID NOS: 1 to 9 and having dipeptide-synthesizing activity is also included in the proteins of the present invention. The homology among amino acid sequences can be determined by using BLAST and FASTA as described above.

It is possible to confirm that the protein of the present invention is a protein having dipeptide-synthesizing activity, for example, in the following manner. That is, a transformant expressing the protein of the present invention is prepared by recombinant DNA techniques, the protein of the present invention is produced using the transformant, and then the protein of the present invention, one or more kinds of amino acids, preferably two kinds of amino acids selected from the group consisting of L-amino acids and glycine, and ATP are allowed to be present in an aqueous medium, followed by HPLC analysis or the like to know whether a dipeptide is formed and accumulated in the aqueous medium.

2. DNAs of the Present Invention

The DNAs of the present invention include:

[1] DNA encoding the protein of the present invention according to [1] to [3] in the above 1;

[2] DNA having the nucleotide sequence shown in any of SEQ ID NOS: 10 to 21; and

[3] DNA which hybridizes with DNA having a nucleotide sequence complementary to the nucleotide sequence shown in any of SEQ ID NOS: 10 to 21 under stringent conditions and which encodes a protein having dipeptide-synthesizing activity.

"To hybridize" refers to a step of hybridization of DNA with DNA having a specific nucleotide sequence or a part of the DNA. Therefore, the nucleotide sequence of the DNA having a specific nucleotide sequence or a part of the DNA may be DNA which is long enough to be useful as a probe for Northern or Southern blot analysis or to be used as an oligonucleotide primer for PCR analysis. DNAs used as a probe include DNAs consisting of at least 100 nucleotides, preferably 200 or more nucleotides, more preferably 500 or more nucleotides, but may also be DNAs consisting of at least 10 nucleotides, preferably 15 or more nucleotides.

The method for hybridization of DNA is well known. The conditions for hybridization can be determined and hybridization experiments can be carried out, for example, according to the methods described in Molecular Cloning, Second Edition, Third Edition (2001); Methods for General and Molecular Bacteriology, ASM Press (1994); Immunology methods manual, Academic press (Molecular), and many other standard textbooks.

Hybridization under the above stringent conditions is carried out, for example, as follows. A filter with DNA immobilized thereon and a probe DNA are incubated in a solution comprising 50% formamide, 5×SSC (750 mM sodium chloride and 75 mM sodium citrate), 50 mM sodium phosphate (pH 7.6), 5×Denhardt's solution, 10% dextran sulfate and 20 µg/l denatured salmon sperm DNA at 42° C. overnight, and after the incubation, the filter is washed in 0.2×SSC solution (ca. 65° C.). Less stringent conditions can also be employed. Modification of the stringent conditions can be made by adjusting the concentration of formamide (the conditions become less stringent as the concentration of formamide is lowered) and by changing the salt concentrations and the temperature conditions. Hybridization under less stringent conditions is carried out, for example, by incubating a filter with DNA immobilized thereon and a probe DNA in a solution comprising 6×SSCE (20×SSCE: 3 mol/l sodium chloride, 0.2 mol/l sodium dihydrogenphosphate and 0.02 mol/l EDTA, pH 7.4), 0.5% SDS, 30% formamide and 100 µg/l denatured salmon sperm DNA at 37° C. overnight, and washing the filter with 1×SSC solution containing 0.1% SDS (50° C.). Hybridization under still less stringent conditions is carried out by using a solution having a high salt concentration (for example, 5×SSC) under the above less stringent conditions, followed by washing.

Various conditions described above can also be established by adding a blocking reagent used to reduce the background of hybridization or changing the reagent. The addition of the above blocking reagent may be accompanied by changes of conditions for hybridization to make the conditions suitable for the purpose.

The above DNA capable of hybridization under stringent conditions includes DNA having at least 80% homology, preferably 90% or more homology, more preferably 94% or more homology, further preferably 98% or more homology, particularly preferably 99% or more homology to the nucleotide sequence of any of the above DNAs as calculated by use of programs such as BLAST and FASTA described above based on the above parameters.

The homology among nucleotide sequences can be determined by using programs such as BLAST and FASTA described above.

It is possible to confirm that the DNA hybridizing with the above DNA under stringent conditions is DNA encoding a protein having dipeptide-synthesizing activity in the following manner. That is, a recombinant DNA expressing the DNA is prepared and a protein is purified from the culture obtained by culturing a microorganism obtained by introducing the recombinant DNA into a host cell. Then, the purified protein as an enzyme source and one or more kinds of amino acids, preferably two kinds of amino acids selected from the group consisting of L-amino acids and glycine are allowed to be present in an aqueous medium, followed by HPLC analysis or the like to know whether a dipeptide is formed and accumulated in the aqueous medium.

3. Microorganisms and Transformants Used in the Production Process of the Present Invention There is not any specific restriction as to the microorganisms and transformants used in the production process of the present invention, so long as they are microorganisms and transformants having the ability to produce the protein of the present invention. Suitable examples of the microorganisms include those belonging to the genus *Ralstonia*, preferably those belonging to *Ralstonia solanacearum*, more preferably *Ralstonia solanacearum* GMI1000, *Ralstonia solanacearum* ATCC 11696, *Ralstonia solanacearum* MAFF 211270, *Ralstonia solanacearum* MAFF 211272, *Ralstonia solanacearum* MAFF 211282, *Ralstonia solanacearum* MAFF 211396, *Ralstonia solanacearum* MAFF 211402, *Ralstonia solanacearum* MAFF 211403, *Ralstonia solanacearum* MAFF 211544, *Ralstonia solanacearum MAFF* 301520, *Ralstonia solanacearum* MAFF 301522, *Ralstonia solanacearum* MAFF 301523 and *Ralstonia solanacearum* MAFF 301526. Suitable examples of the transformants include those transformed with DNA encoding the protein of the present invention.

The above-described *Ralstonia solanacearum* can be obtained from American Type Culture Collection or the gene bank of National Institute of Agrobiological Sciences.

Examples of the transformants transformed with DNA encoding the protein of the present invention are those obtained by transforming a host cell by a known method using a recombinant DNA comprising the DNA of the above 2. Examples of the host cells include procaryotes such as bacterial cells, yeast cells, animal cells, insect cells and plant cells, preferably prokaryotic cells, more preferably bacteria, further preferably microorganisms belonging to the genus *Escherichia.*

4. Preparation of the DNA and the Transformant of the Present Invention

The DNA of the present invention can be obtained, for example, by Southern hybridization of the entire DNA library from a microorganism belonging to the genus *Ralstonia*, preferably a microorganism belonging to *Ralstonia solanacearum*, more preferably *Ralstonia solanacearum* GMI1000, *Ralstonia solanacearum* ATCC 11696, *Ralstonia solanacearum* MAFF 211270, *Ralstonia solanacearum MAFF* 211272, *Ralstonia solanacearum* MAFF 211282, *Ralstonia solanacearum* MAFF 211396, *Ralstonia solanacearum MAFF* 211402, *Ralstonia solanacearum* MAFF 211403, *Ralstonia solanacearum* MAFF 211544, *Ralstonia solanacearum MAFF* 301520, *Ralstonia solanacearum* MAFF 301522, *Ralstonia solanacearum* MAFF 301523 or *Ralstonia solanacearum* MAFF 301526, using a probe designed based on the nucleotide sequence shown in SEQ ID NO: 3 or 4, or by PCR [PCR Protocols, Academic Press (1990)] using primer DNAs designed based on the nucleotide sequence shown in any of SEQ ID NOS: 10 to 21, and as a template, the entire DNA of a microorganism, preferably a microorganism belonging to the genus *Ralstonia*, more preferably a microorganism belonging to *Ralstonia solanacearum*, further preferably *Ralstonia solanacearum* GMI1000, *Ralstonia solanacearum ATCC* 11696, *Ralstonia solanacearum* MAFF 211270, *Ralstonia solanacearum* MAFF 211272, *Ralstonia solanacearum MAFF* 211282, *Ralstonia solanacearum* MAFF 211396, *Ralstonia solanacearum* MAFF 211402, *Ralstonia solanacearum MAFF* 211403, *Ralstonia solanacearum* MAFF 211544, *Ralstonia solanacearum* MAFF 301520, *Ralstonia solanacearum MAFF* 301522, *Ralstonia solanacearum* MAFF 301523 or *Ralstonia solanacearum* MAFF 301526.

The DNA of the present invention or DNA used in the production process of the present invention can also be obtained by conducting a search through various gene sequence databases for a sequence having 85% or more homology, preferably 90% or more homology, more preferably 95% or more homology, further preferably 98% or more homology, particularly preferably 99% or more homology to the nucleotide sequence of DNA encoding the amino acid sequence shown in any of SEQ ID NOS: 1 to 9, and obtaining the desired DNA, based on the nucleotide sequence obtained by the search, from a chromosomal DNA or cDNA library of an organism having the nucleotide sequence according to the above-described method.

The obtained DNA, as such or after cleavage with appropriate restriction enzymes, is inserted into a vector by a conventional method, and the obtained recombinant DNA is introduced into a host cell. Then, the nucleotide sequence of the DNA can be determined by a conventional sequencing method such as the dideoxy method [Proc. Natl. Acad. Sci., USA, 74, 5463 (1977)] or by using a nucleotide sequencer such as 373A DNA Sequencer (Perkin-Elmer Corp.).

In cases where the obtained DNA is found to be a partial DNA by the analysis of nucleotide sequence, the full length DNA can be obtained by Southern hybridization of a chromosomal DNA library using the partial DNA as a probe.

It is also possible to prepare the desired DNA by chemical synthesis using a DNA synthesizer (e.g., Model 8905, PerSeptive Biosystems) based on the determined nucleotide sequence of the DNA.

Examples of the DNAs that can be obtained by the above-described method are DNAs having the nucleotide sequences shown in SEQ ID NOS: 10 to 21.

Examples of the vectors for inserting the DNA of the present invention include pBluescript II KS(+) (Stratagene), pDIRECT [Nucleic Acids Res., 18, 6069 (1990)], pCR-Script Amp SK(+) (Stratagene), pT7Blue (Novagen, Inc.), pCR II (Invitrogen Corp.) and pCR-TRAP (Genhunter Corp.).

As the host cell, microorganisms belonging to the genus *Escherichia*, etc. can be used. Examples of the microorganisms belonging to the genus *Escherichia* include *Escherichia coli* XL1-Blue, *Escherichia coli* XL2-Blue, *Escherichia coli* DH1, *Escherichia* coli MC1000, *Escherichia coli* ATCC 12435, *Escherichia coli* W1485, *Escherichia coli* JM109, *Escherichia coli* HB101, *Escherichia Coli* No. 49, *Escherichia coli* W3110, *Escherichia coli* NY49, *Escherichia coli* MP347, *Escherichia coli* NM522, *Escherichia coli* BL21 and *Escherichia coli* ME8415.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

An example of the transformant of the present invention obtained by the above method is *Escherichia coli* BL21/pRSP1486a, which is a microorganism carrying a recombinant DNA comprising DNA having the sequence shown in SEQ ID NO: 4.

5. Process for Producing the Transformant and the Microorganism Used in the Production Process of the Present Invention On the basis of the DNA of the present invention, a DNA fragment of an appropriate length comprising a region encoding the protein of the present invention is prepared according to need. A transformant having enhanced productivity of the protein can be obtained by replacing a nucleotide in the nucleotide sequence of the region encoding the protein so as to make a codon most suitable for the expression in a host cell.

The DNA fragment is inserted downstream of a promoter in an appropriate expression vector to prepare a recombinant DNA.

A transformant which produces the protein of the present invention can be obtained by introducing the recombinant DNA into a host cell suited for the expression vector.

As the host cell, any bacterial cells, yeast cells, animal cells, insect cells, plant cells, etc. that are capable of expressing the desired gene can be used.

The expression vectors that can be employed are those capable of autonomous replication or integration into the chromosome in the above host cells and comprising a promoter at a position appropriate for the transcription of the DNA of the present invention.

When a procaryote such as a bacterium is used as the host cell, it is preferred that the recombinant DNA comprising the DNA of the present invention is a recombinant DNA which is capable of autonomous replication in the procaryote and which comprises a promoter, a ribosome binding sequence, the DNA of the present invention and a transcription termination sequence. The recombinant DNA may further comprise a gene regulating the promoter.

Examples of suitable expression vectors are pBTrp2, pBTac1 and pBTac2 (products of Boehringer Mannheim GmbH), pHelix1 (Roche Diagnostics Corp.), pKK233-2 (Amersham Pharmacia Biotech), pSE280 (Invitrogen Corp.), pGEMEX-1 (Promega Corp.), pQE-8 (Qiagen, Inc.), pET-3 (Novagen, Inc.), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (Takara Shuzo Co., Ltd.), pUC118 (Takara Shuzo Co., Ltd.) and pPA1 (Japanese Published Unexamined Patent Application No. 233798/88).

As the promoter, any promoters capable of functioning in host cells such as *Escherichia coli* can be used. For example, promoters derived from *Escherichia coli* or phage, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and letI promoter, etc. can also be used.

Also useful are promoters such as xylA promoter for the expression in microorganisms belonging to the genus *Bacillus* [Appl. Microbiol. Biotechnol., 35, 594-599 (1991)] and P54-6 promoter for the expression in microorganisms belonging to the genus *Corynebacterium* [Appl. Microbiol. Biotechnol., 53, 674-679 (2000)].

It is preferred to use a plasmid in which the distance between the Shine-Dalgarno sequence (ribosome binding sequence) and the initiation codon is adjusted to an appropriate length (e.g., 6 to 18 nucleotides).

In the recombinant DNA wherein the DNA of the present invention is ligated to an expression vector, the transcription termination sequence is not essential, but it is preferred to place the transcription termination sequence immediately downstream of the structural gene.

An example of such recombinant DNA is pRSP1486a.

Examples of procaryotes include microorganisms belonging to the genera *Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* and *Zymomonas*. Specific examples are *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21, *Bacillus subtilis* ATCC 33712, *Bacillus megaterium, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 14297, *Corynebacterium acetoacidophilum* ATCC 13870, *Microbacterium ammoniaphilum* ATCC 15354, *Serratia ficaria, Serratia fonticola, Serratia liquefaciens, Serratia marcescens, Pseudomonas* sp. D-0110, *Agrobacterium radlobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globiformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium* sp. ATCC 29409, *Rhodobacter capsulatus, Rhodobacter sphaeroides, Rhodopseudomonas blastica, Rhodopseudomonas marina,*

*Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus* and *Zymomonas mobilis.*

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

When a yeast strain is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast strains can be used. Suitable promoters include PHO5 promoter, PGK promoter, GAP promoter, ADH promoter, gal 1 promoter, gal 10 promoter, heat shock polypeptide promoter, MFα1 promoter and CUP 1 promoter.

Examples of suitable host cells are yeast strains belonging to the genera *Saccharomyces, Schizosaccharomyces, Kluyveromyces, Trichosporon, Schwanniomyces, Pichia* and *Candida*, specifically, *Saccharomyces cerevisiae, Schizosaccharomyces pombe, Kluyveromyces lactis, Trichosporon pullulans, Schwanniomyces alluvius, Pichia pastoris* and *Candida utilis.*

Introduction of the recombinant DNA can be carried out by any of the methods for introducing DNA into yeast, for example, electroporation [Methods Enzymol., 194, 182 (1990)], the spheroplast method [Proc. Natl. Acad. Sci. USA, 81, 4889 (1984)] and the lithium acetate method [J. Bacteriol., 153, 163 (1983)].

When an animal cell is used as the host cell, pcDNAI, pcDM8 (commercially available from Funakoshi Co., Ltd.), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (Invitrogen Corp.), pREP4 (Invitrogen Corp.), pAGE103 [J. Biochem., 101, 1307 (1987)], pAGE210, pAMo, pAMoA, etc. can be used as the expression vector.

As the promoter, any promoters capable of functioning in animal cells can be used. Suitable promoters include the promoter of IE (immediate early) gene of cytomegalovirus (CMV), SV40 early promoter, metallothionein promoter, the promoter of a retrovirus, heat shock promoter, SRα promoter, etc. The enhancer of IE gene of human CMV may be used in combination with the promoter.

Examples of suitable host cells are mouse myeloma cells, rat myeloma cells, mouse hybridomas, human-derived Namalwa cells and Namalwa KJM-1 cells, human embryonic kidney cells, human leukemia cells, African green monkey kidney cells, Chinese hamster-derived CHO cells, and HBT5637 (Japanese Published Unexamined Patent Application No. 299/88).

The mouse myeloma cells include SP2/0 and NS0; the rat myeloma cells include YB2/0; the human embryonic kidney cells include HEK293 (ATCC CRL-1573); the human leukemia cells include BALL-1; and the African green monkey kidney cells include COS-1 and COS-7.

Introduction of the recombinant DNA can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the protein can be produced by using the methods described in Baculovirus Expression Vectors, A Laboratory Manual, W. H. Freeman and Company, New York (1992); Current Protocols in Molecular Biology; Molecular Biology, A Laboratory Manual; Bio/Technology, 6, 47 (1988), etc.

That is, the recombinant gene transfer vector and a baculovirus are cotransfected into insect cells to obtain a recombinant virus in the culture supernatant of the insect cells, and then insect cells are infected with the recombinant virus, whereby the protein can be produced.

The gene transfer vectors useful in this method include pVL1392, pVL1393 and pBlueBacIII (products of Invitrogen Corp.).

An example of the baculovirus is *Autographa californica* nuclear polyhedrosis virus, which is a virus infecting insects belonging to the family *Barathra.*

Examples of the insect cells are ovarian cells of *Spodoptera frugiperda*, ovarian cells of *Trichoplusia ni*, and cultured cells derived from silkworm ovary.

The ovarian cells of *Spodoptera frugiperda* include Sf9 and Sf21 (Baculovirus Expression Vectors, A Laboratory Manual); the ovarian cells of *Trichoplusia ni* include High 5 and BTI-TN-5B1-4 (Invitrogen Corp.); and the cultured cells derived from silkworm ovary include *Bombyx mori* N4.

Cotransfection of the above recombinant gene transfer vector and the above baculovirus into insect cells for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

When a plant cell is used as the host cell, Ti plasmid, tobacco mosaic virus vector, etc. can be used as the expression vector.

As the promoter, any promoters capable of functioning in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

6. Process for Producing the Protein of the Present Invention

The protein of the present invention can be produced by culturing the transformant obtained by the method of the above 5 in a medium, allowing the protein of the present invention to form and accumulate in the culture, and recovering the protein from the culture.

The host of the above transformant for producing the protein of the present invention may be any bacterium, yeast, animal cell, insect cell, plant cell or the like, but is preferably a bacterium, more preferably a microorganism belonging to the genus *Escherichia*, and further preferably a microorganism belonging to *Escherichia coli*.

When the DNA is expressed in yeast, an animal cell, an insect cell or a plant cell, a glycosylated protein can be obtained.

Culturing of the above transformant in a medium can be carried out by conventional methods for culturing the host.

For the culturing of the transformant obtained by using a procaryote such as *Escherichia coli* or a eucaryote such as yeast as the host, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

For the culturing of the transformant obtained by using an animal cell as the host cell, generally employed media such as RPMI1640 medium [J. Am. Med. Assoc., 199, 519 (1967)], Eagle's MEM [Science, 122, 501 (1952)], DMEM [Virology, 8, 396 (1959)] and 199 medium [Proc. Soc. Biol. Med., 73, 1 (1950)], media prepared by adding fetal calf serum or the like to these media, etc. can be used as the medium.

Culturing is usually carried out at pH 6 to 8 at 25 to 40° C. for 1 to 7 days in the presence of 5% $CO_2$.

If necessary, antibiotics such as kanamycin, penicillin and streptomycin may be added to the medium during the culturing.

For the culturing of the transformant obtained by using an insect cell as the host cell, generally employed media such as TNM-FH medium (PharMingen, Inc.), Sf-900 II SFM medium (Life Technologies, Inc.), ExCell 400 and ExCell 405 (JRH Biosciences, Inc.) and Grace's Insect Medium [Nature, 195, 788 (1962)] can be used as the medium.

Culturing is usually carried out at pH 6 to 7 at 25 to 30° C. for 1 to 5 days.

If necessary, antibiotics such as gentamicin may be added to the medium during the culturing.

The transformant obtained by using a plant cell as the host cell may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out at pH 5 to 9 at 20 to 40° C. for 3 to 60 days.

If necessary, antibiotics such as kanamycin and hygromycin may be added to the medium during the culturing.

The protein of the present invention may be produced by intracellular production by host cells, extracellular secretion by host cells or production on outer membranes by host cells. The structure of the protein to be produced may be altered according to the production method.

When the protein of the present invention is produced in host cells or on outer membranes of host cells, it is possible to force the protein to be secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc.

That is, extracellular secretion of the protein of the present invention by host cells can be caused by producing it in the form of a protein in which a signal peptide is added upstream of a protein containing the active site of the protein of the present invention by the use of recombinant DNA techniques.

It is also possible to increase the protein production by utilizing a gene amplification system using a dihydrofolate reductase gene or the like according to the method described in Japanese Published Unexamined Patent Application No. 227075/90.

Further, the protein of the present invention can be produced using an animal having an introduced gene (non-human transgenic animal) or a plant having an introduced gene (transgenic plant) constructed by redifferentiation of animal or plant cells carrying the introduced gene.

When the transformant producing the protein of the present invention is an animal or plant, the protein can be produced by raising or culturing the animal or plant in a usual manner, allowing the protein to form and accumulate therein, and recovering the protein from the animal or plant.

Production of the protein of the present invention using an animal can be carried out, for example, by producing the protein in an animal constructed by introducing the gene according to known methods [Am. J. Clin. Nutr., 63, 639S (1996); Am. J. Clin. Nutr., 63, 627S (1996); Bio/Technology, 9, 830 (1991)].

In the case of an animal, the protein of the present invention can be produced, for example, by raising a non-human transgenic animal carrying the introduced DNA of the present invention or DNA used in the production process of the present invention, allowing the protein to form and accumulate in the animal, and recovering the protein from the animal. The places where the protein is formed and accumulated include milk (Japanese Published Unexamined Patent Application No. 309192/88), egg, etc. of the animal. As the promoter in this process, any promoters capable of functioning in an animal can be used. Preferred promoters include mammary gland cell-specific promoters such as a casein promoter, β casein promoter, β lactoglobulin promoter and whey acidic protein promoter.

Production of the protein of the present invention using a plant can be carried out, for example, by culturing a transgenic plant carrying the introduced DNA encoding the protein of the present invention according to known methods [Soshiki Baiyo (Tissue Culture), 20 (1994); Soshiki Baiyo, 21 (1995); Trends Biotechnol., 15, 45 (1997)], allowing the protein to form and accumulate in the plant, and recovering the protein from the plant.

The protein of the present invention produced by using the transformant producing the protein of the present invention can be isolated and purified by conventional methods for isolating and purifying enzymes.

For example, when the protein of the present invention is produced in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract.

A purified protein preparation can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Chemical Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the protein is produced as an inclusion body in cells, the cells are similarly recovered and disrupted, followed by centrifugation to obtain a precipitate fraction. After the protein is recovered from the precipitate fraction by an ordinary method, the inclusion body of the protein is solubilized with a protein-denaturing agent.

The solubilized protein solution is diluted with or dialyzed against a solution containing no protein-denaturing agent or a solution containing the protein-denaturing agent at such a low concentration that denaturation of protein is not caused, whereby the protein is renatured to have normal higher-order structure. Then, a purified protein preparation can be obtained by the same isolation and purification steps as described above.

When the protein of the present invention or its derivative such as a glycosylated form is extracellularly secreted, the protein or its derivative such as a glycosylated form can be recovered in the culture supernatant.

That is, the culture is treated by the same means as above, e.g., centrifugation, to obtain a soluble fraction. A purified protein preparation can be obtained from the soluble fraction by using the same isolation and purification methods as described above.

Examples of the proteins obtained in the above manner are proteins consisting of the amino acid sequences shown in SEQ ID NOS: 1 and 2.

It is also possible to produce the protein of the present invention as a fusion protein with another protein and to purify it by affinity chromatography using a substance having affinity for the fused protein. For example, the protein of the present invention can be produced as a fusion protein with protein A and can be purified by affinity chromatography using immunoglobulin G according to the method of Lowe, et al. [Proc. Natl. Acad. Sci. USA, 86, 8227 (1989); Genes Develop., 4, 1288 (1990)] and the methods described in Japanese Published Unexamined Patent Application No. 336963/93 and WO94/23021.

The protein of the present invention can also be produced as a fusion protein with a Flag peptide and purified by affinity chromatography using an anti-Flag antibody [Proc. Natl. Acad. Sci. USA, 86, 8227 (1989); Genes Develop., 4, 1288 (1990)], or can be produced as a fusion protein with polyhistidine and purified by affinity chromatography using a metal coordination resin having a high affinity for polyhistidine. Further, the protein can be purified by affinity chromatography using an antibody against the protein itself.

The protein of the present invention can also be produced by chemical synthetic methods such as the Fmoc method (the fluorenylmethyloxycarbonyl method) and the tBoc method (the t-butyloxycarbonyl method) based on the amino acid sequence information on the protein obtained above. Further, the protein can be chemically synthesized by using peptide synthesizers from Advanced ChemTech, Perkin-Elmer, Pharmacia, Protein Technology Instrument, Synthecell-Vega, PerSeptive, Shimadzu Corporation, etc.

7. Process for Producing a Dipeptide of the Present Invention

A dipeptide can be produced by allowing a culture of the microorganism or the transformant of the above 3 or a treated matter of the culture, or the protein of the present invention of the above 1, and one or more kinds of amino acids to be present in an aqueous medium, allowing the dipeptide to form and accumulate in the medium, and recovering the dipeptide from the medium.

(1) Process for producing a Dipeptide Using the Protein of the Present Invention as an Enzyme Source When the protein of the present invention is used as an enzyme source in the production process of the present invention, one or more kinds, preferably one or two kinds of amino acids used as substrates may be any amino acids, preferably amino acids selected from the group consisting of L-amino acids, Gly and β-alanine (β-Ala), which can be used in any combination. Examples of L-amino acids are L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-aminobutyric-acid (L-α-AB), L-azaserine, L-theanine, 4-hydroxy-L-proline (L-4-HYP), 3-hydroxy-L-proline (L-3-HYP), L-ornithine (L-Orn), L-citrulline (L-Cit) and L-6-diazo-5-oxo-norleucine.

The amino acids which are more preferably used in the above production process are one or two kinds of amino acids selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp and β-Ala. Further preferred amino acids are: a combination of L-Ala and one kind of amino acid selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp and β-Ala; a combination of L-Gln and one kind of amino acid selected from the group consisting of Gly, L-Val, L-Ile, L-Phe, L-Met, L-Ser, L-Thr, L-Cys and L-His; a combination of L-Glu and one kind of amino acid selected from the group consisting of L-Phe, L-Met; L-Ser, L-Cys and L-His; a combination of Gly and one kind of amino acid selected from the group consisting of L-Phe, L-Met, L-Ser, L-Cys and L-His; a combination of L-Val and one kind of amino acid selected from the group consisting of L-Phe, L-Met, L-Ser, L-Cys, L-Asn and L-His; a combination of L-Leu and one kind of amino acid selected from the group consisting of L-Phe, L-Met, L-Ser, L-Cys and L-His; a combination of L-Ile and one kind of amino acid selected from the group consisting of L-Phe, L-Met, L-Ser, L-Cys and L-His; a combination of L-Pro and one kind of amino acid selected from the group consisting of L-Phe, L-Met, L-Ser, L-Cys and L-His; a combination of L-Phe and one kind of amino acid selected from the group consisting of L-Phe, L-Trp, L-Met, L-Ser, L-Thr, L-Cys, L-Asn, L-Lys, L-Arg, L-His, L-Asp and β-Ala; a combination of L-Trp and L-Cys; a combination of L-Met and one kind of amino acid selected from the group consisting of L-Met, L-Ser, L-Thr, L-Cys, L-Asn, L-Lys, L-Arg, L-His, L-Asp and β-Ala; a combination of L-Ser and one kind of amino acid selected from the group consisting of L-Met, L-Ser, L-Thr, L-Cys, L-Asn, L-Lys, L-Arg, L-His and β-Ala; a combination of L-Thr and one kind of amino acid selected from the group consisting of L-Cys, L-His and β-Ala; a combination of L-Cys and one kind of amino acid selected from the group consisting of L-Cys, L-Asn, L-Lys, L-Arg, L-His, L-Asp and β-Ala; a combination of L-Asn and L-His; a combination of L-Lys and L-His; a combination of L-Arg and L-His; and a combination of L-His and one kind of amino acid selected from the group consisting of L-His, L-Asp and β-Ala; more preferably, a combination of L-Ala and one kind of amino acid selected from the group consisting of L-Ala, L-Gln, L-Phe, L-Met, L-Ser and L-His; a combination of L-Cys and one kind of amino acid selected from the group consisting of L-Cys, L-Gln, L-Phe and L-Ser; a combination of L-His and one kind of amino acid selected from the group consisting of Gly, L-Leu, L-Met, L-Ser, L-Thr, L-His and L-Val; a combination of L-Phe and L-Phe or L-Val; and a combination of L-Gln and L-Val.

In the above process, the protein of the present invention is added in an amount of 0.01 to 100 mg, preferably 0.1 mg to 10 mg per mg of amino acid used as a substrate.

In the above process, the amino acid used as a substrate is added to the aqueous medium at the start or in the course of reaction to give a concentration of 0.1 to 500 g/l, preferably 0.2 to 200 g/l.

In the above process, ATP can be used as an energy source and is preferably used at a concentration of 0.5 mmol/l to 10 mol/l.

The aqueous medium used in the above process may comprise any components and may have any composition so far as the dipeptide-forming reaction is not inhibited. Suitable aqueous media include water and buffers such as phosphate buffer, carbonate buffer, acetate buffer, borate buffer, citrate buffer and Tris buffer. The aqueous medium may comprise alcohols such as methanol and ethanol, esters such as ethyl acetate, ketones such as acetone, and amides such as acetamide.

The dipeptide-forming reaction is carried out in the aqueous medium at pH 5 to 11, preferably pH 6 to 10, at 20 to 50° C., preferably 25 to 45° C., for 2 to 150 hours, preferably 6 to 120 hours.

The dipeptides produced by the above process include dipeptides in which amino acids, preferably amino acids selected from the group consisting of L-amino acids, Gly and β-Ala, more preferably amino acids selected from the group consisting of L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-Azaserine, L-theanine, L-4-HYP, L-3-HYP, L-Orn, L-Cit, L-6-diazo-5-oxo-norleucine, Gly and β-Ala are linked with each other by a peptide bond. Further preferred are dipeptides in which two amino acids are linked by a peptide bond represented by formula (I):

$$R^1\text{-}R^2 \qquad (I)$$

(wherein when $R^1$ is L-Ala, $R^2$ is an amino acid selected from the group consisting of L-Ala, Gly, L-Val, L-Leu, L-Ile, L-Pro, L-Phe, L-Ser, L-Thr, L-Cys, L-Asn, L-Tyr, L-Lys, L-Arg, L-Asp and β-Ala; when $R^1$ is L-Gln, $R^2$ is an amino acid selected from the group consisting of L-Ala, Gly, L-Val, L-Ile, L-Phe, L-Met, L-Ser, L-Thr, L-Cys and L-His; when $R^1$ is L-Glu, $R^2$ is an amino acid selected from the group consisting of L-Phe, L-Met, L-Ser, L-Cys and L-His; when $R^1$ is Gly, $R^2$ is an amino acid selected from the group consisting of L-Ala, L-Gln, L-Phe, L-Met, L-Ser, L-Cys and L-His; when $R^1$ is L-Val, $R^2$ is an amino acid selected from the group consisting of L-Gln, L-Phe, L-Met, L-Ser, L-Cys, L-Asn and L-His; when $R^1$ is L-Leu, $R^2$ is an amino acid selected from the group consisting of L-Phe, L-Met, L-Ser, L-Cys and L-His; when $R^1$ is L-Ile, $R^2$ is an amino acid selected from the group consisting of L-Gln, L-Phe, L-Met, L-Ser, L-Cys and L-His; when $R^1$ is L-Pro, $R^2$ is an amino acid selected from the group consisting of L-Ala, L-Phe, L-Met, L-Ser, L-Cys and L-His; when $R^1$ is L-Phe, $R^2$ is an amino acid selected from the group consisting of L-Gln, L-Glu, Gly, L-Val, L-Leu, L-Ile, L-Pro, L-Phe, L-Trp, L-Met, L-Ser, L-Thr, L-Cys, L-Asn, L-Lys, L-Arg, L-His, L-Asp and β-Ala; when $R^1$ is L-Trp, $R^2$ is L-Phe or L-Cys; when $R^1$ is L-Met, $R^2$ is an amino acid selected from the group consisting of L-Ala, L-Gln, L-Glu, Gly, L-Val, L-Leu, L-Ile, L-Pro, L-Phe, L-Met, L-Ser, L-Thr, L-Cys, L-Asn, L-Lys, L-Arg, L-His, L-Asp and β-Ala; when $R^1$ is L-Ser, $R^2$ is an amino acid selected from the group consisting of L-Ala, L-Gln, L-Glu, Gly, L-Val, L-Leu, L-Ile, L-Pro, L-Phe, L-Met, L-Ser, L-Thr, L-Cys, L-Asn, L-Lys, L-Arg, L-His and β-Ala; when $R^1$ is L-Thr, $R^2$ is an amino acid selected from the group consisting of L-Ala, L-Gln, L-Phe, L-Met, L-Ser, L-Cys, L-His and β-Ala; when $R^1$ is L-Cys, $R^2$ is an amino acid selected from the group consisting of L-Ala, L-Gln, L-Glu, Gly, L-Val, L-Leu, L-Ile, L-Pro, L-Trp, L-Met, L-Ser, L-Thr, L-Cys, L-Asn, L-Lys, L-Arg, L-His, L-Asp and β-Ala; when $R^1$ is L-Asn, $R^2$ is an amino acid selected from the group consisting of L-Ala, L-Val, L-Phe, L-Met, L-Ser, L-Cys and L-His; when $R^1$ is L-Lys, $R^2$ is an amino acid selected from the group consisting of L-Ala, L-Phe, L-Met, L-Ser, L-Cys and L-His; when $R^1$ is L-Arg, $R^2$ is an amino acid selected from the group consisting of L-Ala, L-Phe, L-Met, L-Ser, L-Cys and L-His; when $R^1$ is L-His, $R^2$ is an amino acid selected from the group consisting of L-Ala, L-Gln, L-Glu, Gly, L-Val, L-Leu, L-Ile, L-Pro, L-Phe, L-Met, L-Ser, L-Thr, L-Cys, L-Asn, L-Lys, L-Arg, L-His, L-Asp and β-Ala; when $R^1$ is L-Asp, $R^2$ is an amino acid selected from the group consisting of L-Ala, L-Phe, L-Met, L-Cys and L-His; and when $R^1$ is β-Ala, $R^2$ is an amino acid selected from the group consisting of L-Ala, L-Phe, L-Met, L-Ser, L-Thr, L-Cys and L-His). Particularly preferred are dipeptides in which two amino acids are linked by a peptide bond represented by formula (I) (wherein when $R^1$ is L-Ala, $R^2$ is an amino acid selected from the group consisting of L-Ala, L-Val, L-Leu, L-Ile, L-Phe and L-Tyr; when $R^1$ is L-Cys, $R^2$ is L-Cys; when $R^1$ is L-Gln, $R^2$ is L-Ala, L-Cys or L-Val; when $R^1$ is L-His, $R^2$ is an amino acid selected from the group consisting of L-Ala, Gly, L-Leu, L-His, L-Met, L-Ser, L-Thr and L-Val; when $R^1$ is L-Met, $R^2$ is L-Ala or L-Met; when $R^1$ is L-Phe, $R^2$ is an amino acid selected from the group consisting of L-Ala, L-Phe, L-Cys and L-Val; and when $R^1$ is L-Ser, $R^2$ is an amino acid selected from the group consisting of L-Ala, L-Ser and L-cys).

(2) Process for Producing a Dipeptide Using a Culture of a Microorganism or a Transformant or a Treated Matter of the Culture as an Enzyme Source Examples of cultures of a microorganism or a transformant used as an enzyme source in the process of the present invention are cultures obtained by culturing the microorganism or transformant by the method of the above 6. Examples of the treated matters of the culture of the microorganism or transformant include concentrated culture, dried culture, cells obtained by centrifuging or filtering the culture, products obtained by subjecting the cells to drying, freeze-drying, treatment with a surfactant, treatment with a solvent and enzymatic treatment, treated matters containing living cells having the same function as the microorganism as an enzyme source, such as a product obtained by subjecting the cells to immobilization, products obtained by subjecting the cells to ultrasonication and mechanical friction, and crude enzyme extracts obtained from such treated cells.

When a culture of a transformant or a microorganism or a treated matter of the culture is used as an enzyme source, one or more kinds of amino acids used as substrates include the same amino acids as in the above (1).

The amount of the enzyme source to be added varies according to its specific activity, etc., but is, for example, 5 to 1000 mg (wet cell weight), preferably 10 to 400 mg per mg of amino acid used as a substrate.

The amino acid used as a substrate can be added to an aqueous medium in the same manner as in the above (1). ATP can be used as an energy source by allowing ATP to be present in an aqueous medium in the same manner as in the above (1).

As the aqueous medium, the media described in the above (1) can be used. In addition, a supernatant of the culture of a microorganism or a transformant used as an enzyme source can also be used as the aqueous medium.

The conditions for the dipeptide-forming reaction are the same as those in the above (1).

Examples of the dipeptides produced by the above process are the same dipeptides as in the above (1).

In the processes described in the above (1) and (2), recovery of the dipeptide formed and accumulated in the aqueous medium can be carried out by ordinary methods using active carbon, ion-exchange resins, etc. or by means such as extraction with an organic solvent, crystallization, thin layer chromatography and high performance liquid chromatography.

Certain embodiments of the present invention are illustrated in the following examples. These examples are not to be construed as limiting the scope of the invention.

EXAMPLE 1

Acquisition of DNA Encoding a Protein Having Dipeptide-Synthesizing Activity and Construction of a Recombinant Strain Expressing the Protein Based on the nucleotide sequence information of RSP1486 gene encoding a function-unknown protein which has the nucleotide sequence shown in SEQ ID NO: 3 existing on the chromosomal DNA of *Ralstonia solanacearum* GMI1000, homologous genes of RSP1486 gene were obtained respectively from the entire DNA (chromosomal DNA and mega plasmid DNA) of *Ralstonia solanacearum* ATCC 11696, *Ralstonia solanacearum* MAFF 211270, *Ralstonia solanacearum* MAFF 211272, *Ralstonia solanacearum* MAFF 211282, *Ralstonia solanacearum* MAFF 211396, *Ralstonia solanacearum* MAFF 211402, *Ralstonia solanacearum* MAFF 211403, *Ralstonia solanacearum* MAFF 211544, *Ralstonia solanacearum* MAFF 301520, *Ralstonia solanacearum* MAFF 301522, *Ralstonia solanacearum* MAFF 301523 and *Ralstonia solanacearum* MAFF 301526 in the following manner.

The above strains were respectively spread on YPGA medium[7 g/l yeast extract (Difco), 7 g/l Bacto-peptone (Difco), 7 g/l glucose and 1.5 g/l agar] and subjected to stationary culture overnight at 30° C. One platinum loop of grown cells was inoculated into 3 ml of YPG medium[7 g/l yeast extract (Difco), 7 g/l Bacto-peptone (Difco) and 7 g/l glucose], followed by shaking culture at 30° C. for 24 hours. The cells were collected by centrifugation, and a mixture of chromosomal DNA and mega plasmid was prepared from the cells using DNeasy Kit (Qiagen, Inc.).

DNAs having the nucleotide sequences shown in SEQ ID NOS: 22 and 23 (hereinafter referred to as primer A and primer B, respectively) were synthesized by using a DNA synthesizer (Model 8905, PerSeptive Biosystems, Inc.). Primer A has a nucleotide sequence wherein a sequence containing the NdeI recognition sequence is added to the 5' end of a region containing the initiation codon of the RSP1486 gene on the chromosomal DNA of *Ralstonia solanacearum* GMI1000. Primer B has a nucleotide sequence wherein a sequence containing the XhoI recognition sequence is added to the 5' end of a nucleotide sequence complementary to a DNA sequence containing the N terminal amino acid sequence of the RSP1486 gene.

PCR was carried out for amplification of a fragment of a homologous gene of the RSP1486 gene using the above primer A and primer B and the entire DNA of each of the above *Ralstonia solanacearum* strains as a template. PCR was carried out using 50 μl of a reaction mixture comprising 0.1 μg of the entire DNA, 0.5 μmol/l each of the primers, 2 units of KOD plus DNA polymerase (Toyobo Co., Ltd.), 5 μl of buffer for KOD plus DNA polymerase (10×) (Toyobo Co., Ltd.) and 200 μmol/l each of dNTPs (DATP, dGTP, dCTP and dTTP) under the following conditions: incubation at 95° C. for 2 minutes; 30 cycles of 95° C. for 15 seconds, 53° C. for 30 seconds and 68° C. for one minute; and a final incubation at 68° C. for 2 minutes.

One-tenth of each of the resulting reaction mixtures was subjected to agarose gel electrophoresis to confirm that a ca. 1.4 kb DNA fragment corresponding to the fragment of the homologous gene of RSP1486 gene was amplified by the PCR. Then, the DNA fragment was purified from the remaining reaction mixture using GFX-PCR and Gel Band purification kit (Amersham) and dissolved in 20 μl of TE.

The nucleotide sequence of each DNA was determined by a known method, whereby it was confirmed that the following DNAs were isolated: DNA having the nucleotide sequence shown in SEQ ID NO: 11 encoding the amino acid sequence shown in SEQ ID NO: 2 from *Ralstonia solanacearum* ATCC 11696; DNA having the nucleotide sequence shown in SEQ ID NO: 12 encoding the amino acid sequence shown in SEQ ID NO: 3 from *Ralstonia solanacearum* MAFF 211270; DNA having the nucleotide sequence shown in SEQ ID NO: 13 encoding the amino acid sequence shown in SEQ ID NO: 4 from *Ralstonia solanacearum* MAFF 211272; DNA having the nucleotide sequence shown in SEQ ID NO: 14 encoding the amino acid sequence shown in SEQ ID NO: 3 from *Ralstonia solanacearum* MAFF 211282; DNA having the nucleotide sequence shown in SEQ ID NO: 14 encoding the amino acid sequence shown in SEQ ID NO: 3 from *Ralstonia* solanacearum MAFF 211396; DNA having the nucleotide sequence shown in SEQ ID NO: 15 encoding the amino acid sequence shown in SEQ ID NO: 5 from *Ralstonia solanacearum* MAFF 211402; DNA having the nucleotide sequence shown in SEQ ID NO: 16 encoding the amino acid sequence shown in SEQ ID NO: 6 from *Ralstonia solanacearum* ATCC MAFF 211403; DNA having the nucleotide sequence shown in SEQ ID NO: 17 encoding the amino acid sequence shown in SEQ ID NO: 7 from *Ralstonia solanacearum* MAFF 211544; DNA having the nucleotide sequence shown in SEQ ID NO: 18 encoding the amino acid sequence shown in SEQ ID NO: 8 from *Ralstonia solanacearum* MAFF 301520; DNA having the nucleotide sequence shown in SEQ ID NO: 19 encoding the amino acid sequence shown in SEQ ID NO: 9 from *Ralstonia solanacearum* MAFF 301522; DNA having the nucleotide sequence shown in SEQ ID NO: 20 encoding the amino acid sequence shown in SEQ ID NO: 8 from *Ralstonia solanacearum* MAFF 301523; and DNA having the nucleotide sequence shown in SEQ ID NO: 21 encoding the amino acid sequence shown in SEQ ID NO: 8 from *Ralstonia solanacearum* MAFF 301526. The amino acid sequence of RSP1486 protein shown in SEQ ID NO: 1 and the amino acid sequence shown in SEQ ID NO: 2 were compared and it was confirmed that they share 94.7% identity.

Each of the above-obtained DNA solutions (5 μl) was subjected to reaction to cleave the DNA with restriction enzymes NdeI and XhoI. DNA fragments were separated by agarose gel electrophoresis, and a ca. 1.4 kb DNA fragment containing a homologous gene of the RSP1486 gene was recovered using GFX-PCR and Gel Band purification kit.

Expression vector pET-21a(+) (Novagen, Inc.) (0.2 μg) was cleaved with restriction enzymes NdeI and XhoI. DNA fragments were separated by agarose gel electrophoresis, and a ca. 5.4 kb DNA fragment was recovered in the same manner as above.

Each of the above-obtained ca. 1.4 kb DNA fragments containing a homologous gene of the RSP1486 gene and the ca. 5.4 kb DNA fragment of expression vector pET-21a(+) obtained above were subjected to ligation reaction using a ligation kit (Takara Bio Inc.) at 16° C. for 16 hours.

*Escherichia coli* DH5a (Takara Bio Inc.) was transformed using each reaction mixture according to the method using calcium ion [Proc. Natl. Acad. Sci. USA, 69, 2110 (1972)], spread on LB agar medium containing 50 μg/ml ampicillin, and cultured overnight at 30° C.

A plasmid was extracted from a colony of each transformant that grew on the medium according to a known method, and the structure of each plasmid was analyzed using restriction enzymes. As a result, it was confirmed that an expression vector in which a homologous gene of the RSP1486 gene having His-tag added to the N terminus was ligated downstream of the T7 promoter was obtained. The homologous gene of the RSP1486 gene derived from *Ralstonia solanacearum* ATCC 11696 was designated as RSP1486a gene and the expression vector containing the gene was designated as pRSP1486a (FIG. 1).

*Escherichia coli* BL21(DE3) (Novagen, Inc.) was transformed using pRSP1486a according to the method using calcium ion, spread on LB agar medium containing 50 μg/ml ampicillin, and cultured overnight at 30° C.

A plasmid was extracted from a colony of the transformant that grew on the medium according to a known method, and the structure of the plasmid was analyzed using restriction enzymes, whereby it was confirmed that the plasmid carried pRSP1486a.

EXAMPLE 2

Production of a Protein Having Dipeptide-Synthesizing Activity

*Escherichia coli* BL21(DE3) carrying pRSP1486a (*Escherichia coli* BL21(DE3)/pRSP1486a) obtained in Example 1 was inoculated into 3 ml of LB medium containing 50 μg/ml ampicillin in a test tube, and subjected to shaking culture at 37° C. for 6 hours. A portion of the resulting culture (100 μl) was inoculated into 100 ml of LB medium in a 500-ml Erlenmeyer flask and subjected to shaking culture at 37° C. for 3 hours. Then, isopropyl-β-D-thiogalactopyranoside (IPTG) was added to give a final concentration of 1 mmol/l, followed by further shaking culture at 28° C. for 15 hours. The resulting culture was centrifuged to obtain wet cells.

The wet cells were disrupted by ultrasonication and then centrifuged to obtain a supernatant. A His-tagged protein was purified from the obtained supernatant using HisTrap (His-tagged protein purification kit, Amersham).

EXAMPLE 3

Production of Dipeptides Using the His-Tagged Protein

Reaction mixtures comprising the purified His-tagged protein obtained in Example 2 (65 μg/l), 50 mmol/l Tris-HCl buffer (pH 8.0), 12.5 mmol/l magnesium sulfate, 12.5 mmol/l ATP, and respective combinations of L-amino acids, Gly and β-Ala shown in the first row and the leftmost column of Table 2 (12.5 mmol/l each) were prepared, and the resulting mixtures were subjected to reaction at 30° C. for 11 hours. After the completion of reactions, the amount of phosphoric acid liberated in the reaction mixtures was determined using Determiner LIP (Kyowa Medex Co., Ltd.) to confirm the progress of reactions. The reaction products were derivatized with FMOC (fluorenylmethyl chloroformate) and then analyzed by HPLC, whereby it was confirmed that the dipeptides shown in Table 1 were formed.

Derivatization with FMOC was carried out by mixing the above reaction mixture (30 μl) with 0.1 mol/l borate buffer (270 μl, adjusted to pH 9.0 with sodium hydroxide), adding 1.5 mg/ml FMOC solution in acetone (300 μl) thereto, and subjecting the resulting mixture to reaction at room temperature for 40 minutes. After the completion of the reaction, 600 μl of a 25% (v/v) acetonitrile solution (0.25 mol/l borate buffer of pH 5.5) was added to the reaction mixture to prepare a sample for HPLC analysis.

HPLC analysis was carried out basically under the following conditions, but the pH of solution A below and the concentration gradient schedule were appropriately modified according to the dipeptide to be detected.

Separation column: Develosil ODS-HG-5 (Nomura Kagaku Co., Ltd.)

Mobile phase:

Solution A: 20 mmol/l ammonium hydrogenphosphate solution (adjusted to pH 6.5 with aqueous ammonia) and methanol (85:15)

Solution B: acetonitrile and water (9:1)

The ratio of solution A to solution B (A:B ratio) was 75:25 during the first 2 minutes of analysis; from minute 2 to minute 21, the ratio of solution B was increased with a linear gradient so that the A:B ratio became 55:45 at minute 21; from minute 21 to minute 36, the ratio of solution B was increased with a linear gradient so that the A:B ratio became 45:55 at minute 36; from minute 36 to minute 37, the ratio of solution B was increased with a linear gradient so that the A:B ratio became 1:99 at minute 37; from minute 37 to minute 39, the A:B ratio was maintained at 1:99; from minute 39 to minute 44, the ratio of solution B was decreased with a linear gradient so that the A:B ratio became 82:18 at minute 44; and from minute 44 to minute 50, the A:B ratio was made 75:25.

Flow rate: 1.0 ml/min
Column temperature: 35° C.
Detection:
Excitation wavelength: 254 nm
Luminescence wavelength: 630 nm

TABLE 1

Table 1-1

| | Ala | Gln | Glu | Gly | Val | Leu | Ile | Pro |
|---|---|---|---|---|---|---|---|---|
| Ala | AlaAla | GlnAla AlaAla | AlaAla | ○ | AlaVal AlaAla | AlaLeu AlaAla | AlaIle AlaAla | ○ |
| Gln | | | | ○ | ○ | | ○ | |
| Glu | | | | | | | | |
| Gly | | | | | | | | |
| Val | | | | | | | | |
| Leu | | | | | | | | |
| Ile | | | | | | | | |
| Pro | | | | | | | | |
| Phe | | | | | | | | |
| Trp | | | | | | | | |
| Met | | | | | | | | |
| Ser | | | | | | | | |
| Thr | | | | | | | | |
| Cys | | | | | | | | |
| Asn | | | | | | | | |
| Tyr | | | | | | | | |
| Lys | | | | | | | | |
| Arg | | | | | | | | |
| His | | | | | | | | |
| Asp | | | | | | | | |
| β-Ala | | | | | | | | |

Table 1-2

| | Phe | Trp | Met | Ser | Thr | Cys | Asn | Tyr |
|---|---|---|---|---|---|---|---|---|
| Ala | AlaPhe AlaAla ○ | AlaAla | AlaAla ○ | ○ | ○ | ○ | ○ | AlaTyr AlaAla |
| Gln | ○ | | ○ | ○ | ○ | ○ | | |
| Glu | ○ | | ○ | ○ | | ○ | | |
| Gly | ○ | | ○ | ○ | | ○ | | |
| Val | ○ | | ○ | ○ | | ○ | ○ | |
| Leu | ○ | | ○ | ○ | | ○ | | |
| Ile | ○ | | ○ | ○ | | ○ | | |
| Pro | ○ | | ○ | ○ | | ○ | | |
| Phe | ○ | ○ | ○ | ○ | ○ | ○ | ○ | |
| Trp | | | | | | ○ | | |
| Met | | | ○ | ○ | ○ | ○ | ○ | |
| Ser | | | | ○ | ○ | ○ | ○ | |
| Thr | | | | | | ○ | | |
| Cys | | | | | | ○ | ○ | |
| Asn | | | | | | | | |
| Tyr | | | | | | | | |
| Lys | | | | | | | | |
| Arg | | | | | | | | |
| His | | | | | | | | |
| Asp | | | | | | | | |
| β-Ala | | | | | | | | |

TABLE 1-continued

Table1-3

|     | Lys | Arg | His | Asp | β-Ala |
|-----|-----|-----|-----|-----|-------|
| Ala | ○ | ○ | ○ | ○ | ○ |
| Gln |   |   | ○ |   |   |
| Glu |   |   | ○ |   |   |
| Gly |   |   | ○ |   |   |
| Val |   |   | ○ |   |   |
| Leu |   |   | ○ |   |   |
| Ile |   |   | ○ |   |   |
| Pro |   |   | ○ |   |   |
| Phe | ○ | ○ | ○ | ○ | ○ |
| Trp |   |   |   |   |   |
| Met | ○ | ○ | ○ | ○ | ○ |
| Ser | ○ | ○ | ○ |   | ○ |
| Thr |   |   | ○ |   | ○ |
| Cys | ○ | ○ | ○ | ○ | ○ |
| Asn |   |   | ○ |   |   |
| Tyr |   |   |   |   |   |
| Lys |   |   | ○ |   |   |
| Arg | — |   | ○ |   |   |
| His | — | — | ○ | ○ | ○ |
| Asp | — | — | — |   |   |
| β-Ala | — | — | — | — |   |

In the tables, ○ indicates that a product was confirmed though its structure could not be specified by HPLC, and a blank cell indicates that reaction was not carried out.

As shown in Table 1, it was revealed that the protein of the present invention has the activity to form various kinds of dipeptides by linking one or two kinds of amino acids by a peptide bond.

In the same manner as above, proteins encoded by the homologous genes of the RSP1486 gene derived from *Ralstonia solanacearum* MAFF 211270, *Ralstonia solanacearum* MAFF 211272, *Ralstonia solanacearum* MAFF 211282, *Ralstonia solanacearum* MAFF 211396, *Ralstonia solanacearum* MAFF 211402, *Ralstonia solanacearum* MAFF 211403, *Ralstonia solanacearum* MAFF 211544, *Ralstonia solanacearum* MAFF 301520, *Ralstonia solanacearum* MAFF 301522, *Ralstonia solanacearum* MAFF 301523 and *Ralstonia solanacearum* MAFF 301526 were respectively purified and subjected to dipeptide-synthesizing reaction. As a result, it was confirmed that every gene product was a protein having dipeptide-synthesizing activity which has the same substrate specificity as the dipeptide-synthesizing enzyme derived from *Ralstonia solanacearum* ATCC 11696 shown in Table 1.

EXAMPLE 4

Analysis of the Structure of Dipeptides

Of the dipeptides formed in Example 3, the dipeptides shown in Table 2 were subjected to MS analysis, NMR analysis and CE-MS analysis. Their structures were confirmed and their amounts formed were calculated from the integral of 1 mmol/l TSP ([2,2,3,3-D4]sodium 3-3-(trimethylsilyl)propanoate) used as the inner standard in NMR analysis.

TABLE 2

| | Ala | Cys | Gly | Leu | Met | Phe | Ser | Thr | Val |
|---|---|---|---|---|---|---|---|---|---|
| Ala | Ala-Ala 10.1 | | | | | | | | |
| Cys | | Cys-Cys 8.3 | | | | | | | |
| Gln | Gln-Ala 8.9<br>Ala-Ala 2.5 | Gln-Cys 6.8<br>Cys-Cys 0.6 | | | | | | | Gln-Val 5.7 |
| His | His-Ala 10.9<br>Ala-Ala 1.2 | | His-Gly 8.8<br>His-His 0.6 | His-Leu 7.0<br>His-His 0.5 | His-Met 8.5<br>His-His 0.8<br>Met-Met 1.7 | | His-Ser 6.2<br>His-His 0.8<br>Ser-Ser | His-Thr 5.7<br>His-His 1.3 | His-Val 8.8<br>His-His 0.1 |
| Met | Met-Ala 8.7<br>Met-Met<br>Ala-Ala 2.6 | | | | | | | | |

TABLE 2-continued

|  | Ala | Cys | Gly | Leu | Met | Phe | Ser | Thr | Val |
|---|---|---|---|---|---|---|---|---|---|
| Phe | Phe-Ala 8.7 | Phe-Cys 11.5 |  |  |  | Phe-Phe 8.3 |  |  | Phe-Val 5.8 |
|  | Phe-Phe 0.9 | Phe-Phe 1.3 |  |  |  |  |  |  | Phe-Phe 2.6 |
|  | Ala-Ala 2.0 | Cys-Cys |  |  |  |  |  |  |  |
| Ser | Ser-Ala 6.5 | Ser-Cys 6.7 |  |  |  |  |  |  |  |
|  | Ser-Ser | Ser-Ser |  |  |  |  |  |  |  |
|  | Ala-Ala 2.6 | Cys-Cys |  |  |  |  |  |  |  |

The dipeptides formed by reaction using, as substrates, two kinds (or one kind) of L-amino acids or Gly shown in the first row and the leftmost column of Table 2 are shown in the cells of the table, and their amounts formed (mmol/l) are shown below their names. A blank cell indicates that a test was not carried out. When the amount of a dipeptide is not shown below its name, it indicates that the structure of the dipeptide was confirmed but its amount formed was not measured.

INDUSTRIAL APPLICABILITY

In accordance with the present invention, various kinds of dipeptides can be produced inexpensively.

SEQUENCE LISTING FREE TEXT

SEQ ID NO: 22—Description of Artificial Sequence: Synthetic DNA

SEQ ID NO: 23—Description of Artificial Sequence: Synthetic DNA

SEQUENCE LISTING

PCT Process for Producing Dipeptides 20060307 151908 4.txt

The invention claimed is:

1. A process for producing a dipeptide which comprises the steps of:
obtaining an isolated protein having dipeptide-synthesizing activity according to any of the following [1] to [3]:
[1] a protein comprising the amino acid sequence of SEQ ID NO:1, [2] a protein consisting of an amino acid sequence wherein at most twenty amino acid residues are deleted, substituted or added as compared to the amino acid sequence of SEQ ID NO:1, or [3] a protein consisting of an amino acid sequence which has 90% or more homology to the amino acid sequence of SEQ ID NO:1;
combining the isolated protein and one or more kinds of amino acids in an aqueous medium, wherein said one or more kinds of amino acids are selected from the group consisting of L-amino acids, glycine and β-alanine, at least one of said amino acids being an L-amino acid;
allowing the dipeptide to form and accumulate in the medium; and
recovering the dipeptide from the medium, wherein
said dipeptide consists of two members independently selected from the group consisting of L-amino acids, glycine and β-alanine, at least one of said two members being said L-amino acid.

2. A process for producing a dipeptide which comprises the steps of:
obtaining an isolated transformed cell transformed with exogenous recombinant DNA encoding a protein having dipeptide-synthesizing activity according to any of the following [1] to [3]: [1] a protein comprising the amino acid sequence of SEQ ID NO:1, [2] a protein consisting of an amino acid sequence wherein at most twenty amino acid residues are deleted, substituted or added as compared to the amino acid sequence of SEQ ID NO:1, or [3] a protein consisting of an amino acid sequence which has 90% or more homology to the amino acid sequence of SEQ ID NO:1;
combining a culture of the transformant or a treated matter of the culture, said treated matter retaining said protein having said dipeptide-synthesizing activity, and one or more kinds of amino acids in an aqueous medium, wherein said one or more kinds of amino acids are selected from the group consisting of L-amino acids, glycine and β-alanine, at least one of said amino acids being an L-amino acid;
allowing the dipeptide to form and accumulate in the medium; and
recovering the dipeptide from the medium, wherein
the treated matter of the culture is a concentrated culture, a dried culture, cells obtained by centrifuging or filtering the culture, dried cells, freeze-dried cells, surfactant-treated cells, solvent-treated cells, enzyme-treated cells, immobilized cells, ultrasonicated cells, cells treated with mechanical friction or enzyme extracts obtained therefrom, and
said dipeptide consists of two members independently selected from the group consisting of L-amino acids, glycine and β-alanine, at least one of said two members being said L-amino acid.

3. The process according to claim 2, wherein said DNA has the nucleotide sequence of SEQ ID NO:10.

4. The process according to claim 2, wherein said DNA hybridizes with the full complementary sequence of SEQ ID NO:10 in a solution comprising 50% formamide, 5×SSC, 50 mM sodium phosphate, (pH 7.6), 5×Denhardt's solution, 10% dextran sulfate and 20 µg/l denatured salmon sperm DNA at 42° C. overnight followed by washing with 0.2×SSC at 65° C., and which encodes a protein having dipeptide-synthesizing activity.

5. The process according to claim 2, wherein the transformant is a microorganism belonging to the genus Escherichia.

6. The process according to any one of claim 1 to 4 or 5, wherein said one or more kinds of amino acids are:
(i) a combination of L-Ala and an amino acid selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp and β-Ala;
(ii) a combination of L-Gln and an amino acid selected from the group consisting of Gly, L-Val, L-Ile, L-Phe, L-Met, L-Ser, L-Thr, L-Cys and L-His;
(iii) a combination of L-Glu and an amino acid selected from the group consisting of L-Phe, L-Met, L-Ser, L-Cys and L-His;
(iv) a combination of Gly and an amino acid selected from the group consisting of L-Phe, L-Met, L-Ser, L-Cys and L-His;
(v) a combination of L-Val and an amino acid selected from the group consisting of L-Phe, L-Met, L-Ser, L-Cys, L-Asn and L-His;
(vi) a combination of L-Leu and an amino acid selected from the group consisting of L-Phe, L-Met, L-Ser, L-Cys and L-His;

(vii) a combination of L-Ile and an amino acid selected from the group consisting of L-Phe, L-Met, L-Ser, L-Cys and L-His;
(viii) a combination of L-Pro and an amino acid selected from the group consisting of L-Phe, L-Met, L-Ser, L-Cys and L-His;
(ix) a combination of L-Phe and an amino acid selected from the group consisting of L-Phe, L-Trp, L-Met, L-Ser, L-Thr, L-Cys, L-Asn, L-Lys, L-Arg, L-His, L-Asp and β-Ala;
(x) a combination of L-Trp and L-Cys;
(xi) a combination of L-Met and an amino acid selected from the group consisting of L-Met, L-Ser, L-Thr, L-Cys, L-Asn, L-Lys, L-Arg, L-His, L-Asp and β-Ala;
(xii) a combination of L-Ser and an amino acid selected from the group consisting of L-Met, L-Ser, L-Thr, L-Cys, L-Asn, L-Lys, L-Arg, L-His and β-Ala;
(xiii) a combination of L-Thr and an amino acid selected from the group consisting of L-Cys, L-His and β-Ala;
(xiv) a combination of L-Cys and an amino acid selected from the group consisting of L-Cys, L-Asn, L-Lys, L-Arg, L-His, L-Asp and β-Ala;
(xv) a combination of L-Asn and L-His;
(xvi) a combination of L-Lys and L-His;
(xvii) a combination of L-Arg and L-His; and
(xviii) a combination of L-His and an amino acid selected from the group consisting of L-His, L-Asp and β-Ala.

* * * * *

UNITED STATES PATENT AND TRADEMARK OFFICE
CERTIFICATE OF CORRECTION

PATENT NO. : 9,081,199 B2
APPLICATION NO. : 11/817905
DATED : July 14, 2015
INVENTOR(S) : Kuniki Kino et al.

Page 1 of 1

It is certified that error appears in the above-identified patent and that said Letters Patent is hereby corrected as shown below:

In the Claims

COLUMN 10:

Line 53, "*radlobacter,*" should read --*radiobacter*,--.

COLUMN 20:

Line 18, "DNeasy Kit" should read --Dneasy Kit--.

COLUMN 21:

Line 43, "DH5a" should read --DH5α--.

COLUMN 88:

Line 45, "claim 1 to 4 or 5," should read --claims 1 to 5,--.

Signed and Sealed this
Ninth Day of February, 2016

Michelle K. Lee
*Director of the United States Patent and Trademark Office*

```
                        SEQUENCE LISTING

<160> NUMBER OF SEQ ID NOS: 23

<210> SEQ ID NO 1
<211> LENGTH: 449
<212> TYPE: PRT
<213> ORGANISM: Ralstonia solanacearum GMI1000 and Ralstonia
      solanacearum MAFF301560

<400> SEQUENCE: 1

Met Ser Lys Lys Ile Leu Tyr Val Tyr Ala Pro Ala Gly Pro Pro Leu
  1               5                  10                  15

Asp Tyr Cys Phe Pro Lys Ile Ala Ala Arg Gly Glu Val His Thr Cys
                 20                  25                  30

Ile Val Ser Pro Pro Ser Ala Ser Asn Met Glu Ile Leu Arg Arg His
             35                  40                  45

Ser Arg Ala Val His Asp Phe Ser His Val Ala Pro Ala Gln Ala Leu
         50                  55                  60

Glu Gln Val Arg Ala Leu Ala Gln Gln Ile Gly Pro Asp Ala Ile Phe
 65                  70                  75                  80

Thr Phe Ser Glu Phe Leu Leu Lys Ser Val Ser Glu Leu Ala Ala Glu
                 85                  90                  95

Phe Gly Leu Arg Ala Val Gly Pro Asn Ile Ala Leu Gly Arg Asn Lys
                100                 105                 110

Val Leu Met Arg Glu Arg Trp His Gln Ala Gly Ile Pro Gln Pro Ala
            115                 120                 125

Phe Arg Ala Val Arg Ser Glu Gln Glu Ile Ser Arg Val Ala Glu Leu
        130                 135                 140

Asn Phe Pro Val Leu Val Lys Leu Ala Tyr Gly Ala Gly Ser Ile Gly
145                 150                 155                 160

Gln Gln Ile Val Asn Gly Met Asp Glu Leu Pro Ala Ala Ile Glu Arg
                165                 170                 175
```

```
Leu Ile Ala Ala Thr Glu Ala Arg Arg Ala Gly Lys His Glu Phe
            180                 185                 190

Ser Glu His Glu Gly Phe Pro Gln Leu Ile Ala Glu Ile Ile Gln
            195                 200                 205

Ser Thr Thr Thr Ser Trp Tyr Asp Glu Asp Gly Tyr Gly Asp Tyr Leu
210                 215                 220

Ser Val Glu Gly Leu Val Arg Asp Gly Val Tyr Tyr Pro Leu Ala Met
225                 230                 235                 240

Thr Gly Arg Leu Arg Thr Ile Ala Pro Phe Thr Glu Leu Gly Asn Val
                245                 250                 255

Ala Pro Cys Val Leu Ser Thr Asp Lys Lys Ala Lys Ile Val Ala Leu
            260                 265                 270

Ile Lys Arg Ser Ile Asp Ala Leu Gly Phe Glu Asn Cys Ala Thr His
        275                 280                 285

Thr Glu Leu Lys Leu Met Ala Asp Gly Glu Val Ser Phe Leu Glu Thr
            290                 295                 300

Ala Ala Arg Met Gly Gly Val Ala Ile Ala Lys Glu Leu Asp Glu Val
305                 310                 315                 320

Phe Gly Ile Asp Tyr Val Asp Leu Phe Leu Ser Val Ile Leu Gly Glu
                325                 330                 335

Pro Glu Thr Ile Pro Ala Phe Glu Gln Asn Ala Pro Arg Cys Ala Ala
            340                 345                 350

Ala Ser Val Ala Leu Ile Ala Cys Asp Ser Arg Gly Thr Pro Trp Gln
            355                 360                 365

Ser Thr Arg Gly Phe Ala Pro Glu Arg Val Asn Trp Gly Glu Leu Leu
    370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Gly Leu Met Asn Tyr
                405                 410                 415

Ala Gly Gln Ala Phe Leu Val Ser Pro Thr Pro Ala Glu Leu Lys Arg
            420                 425                 430

Ala Ala Tyr Gln Leu Leu Asp Gly Leu Glu Gln Arg Leu Pro Leu His
            435                 440                 445

Ser

<210> SEQ ID NO 2
<211> LENGTH: 449
<212> TYPE: PRT
<213> ORGANISM: Rastonia solanacearum ATCC11696

<400> SEQUENCE: 2

Met Ser Lys Lys Ile Leu Tyr Val Tyr Ala Pro Ala Gly Pro Pro Leu
1               5                   10                  15

Asp Tyr Cys Phe Pro Lys Ile Ala Ala Arg Gly Asp Val His Thr Cys
            20                  25

```
Phe Gly Leu Arg Thr Val Gly Pro Ser Ile Glu Leu Gly Arg Asn Lys
             100                 105                 110

Val Leu Met Arg Glu Arg Trp Gln Gln Ala Gly Ile Pro Gln Pro Ala
         115                 120                 125

Phe Arg Ala Ile Arg Ser Glu Gln Glu Val Ser Arg Val Ala Glu Leu
     130                 135                 140

Asn Phe Pro Val Leu Val Lys Leu Ala Tyr Gly Ala Gly Ser Ile Gly
145                 150                 155                 160

Gln Gln Ile Val Asn Gly Met Asp Glu Leu Pro Ala Ala Ile Ala Arg
                 165                 170                 175

Leu Ile Ala Ala Thr Glu Ala Ala Arg Lys Ala Gly Lys His Glu Phe
             180                 185                 190

Ser Glu His Glu Gly Phe Pro Gln Leu Ile Ala Glu Ile Ile Gln
         195                 200                 205

Ser Thr Thr Ala Ser Trp Tyr Asp Glu Asp Gly Tyr Gly Asp Tyr Leu
     210                 215                 220

Ser Val Glu Gly Leu Val Arg Asp Gly Val Tyr Tyr Pro Leu Ala Met
225                 230                 235                 240

Thr Gly Arg Leu Arg Thr Ile Ala Pro Phe Thr Glu Leu Gly Asn Val
                 245                 250                 255

Ala Pro Cys Val Leu Ser Ala Asp Lys Lys Ala Lys Ile Val Ala Leu
             260                 265                 270

Ile Lys Arg Ala Ile Asp Ala Leu Gly Phe Glu Asn Cys Ala Thr His
         275                 280                 285

Thr Glu Leu Lys Leu Met Ala Asp Gly Glu Val Ser Phe Leu Glu Thr
     290                 295                 300

Ala Ala Arg Met Gly Gly Val Ala Ile Ala Lys Glu Leu Asp Glu Val
305                 310                 315                 320

Phe Gly Leu Asp Tyr Val Asp Leu Phe Leu Gly Val Ile Leu Gly Glu
                 325                 330                 335

Pro Glu Ala Ile Pro Ala Phe Glu Gln Asn Ala Pro Arg Cys Ala Ala
             340                 345                 350

Ala Ser Val Ala Leu Ile Ala Cys Asp Ser Pro Gly Thr Pro Trp Lys
         355                 360                 365

Ser Thr Arg Gly Phe Ala Pro Glu Arg Val Asn Trp Gly Glu Leu Leu
     370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Gly Leu Met Asn Tyr
                 405                 410                 415

Ala Gly Gln Val Phe Leu Val Ser Pro Thr Pro Ala Lys Leu Lys Arg
             420                 425                 430

Ala Ala Tyr Gln Leu Leu Asp Gly Leu Glu Gln Arg Leu Pro Leu His
         435                 440                 445

Ser

<210> SEQ ID NO 3
<211> LENGTH: 449
<212> TYPE: PRT
<213> ORGANISM: Ralstonia solanacearum MAFF211270, Ralstonia
      solanacearum MAFF211282 and Ralstonia solanacearum MAFF211396

<400> SEQUENCE: 3

Met Ser Lys Lys Ile Leu Tyr Val Tyr Ala Pro Ala Gly Pro Pro Leu
1               5                   10                  15
```

```
Asp Tyr Cys Phe Pro Lys Ile Ala Ala Arg Gly Glu Val His Thr Cys
             20                  25                  30
Ile Val Ser Pro Pro Ser Ala Ser Asn Met Glu Ile Leu Arg Arg His
             35                  40                  45
Ser Arg Ala Val His Asp Phe Ser His Val Ala Pro Ala Gln Ala Leu
 50                  55                  60
Glu Gln Val Arg Ala Leu Ala Gln Gln Ile Gly Pro Asp Ala Ile Phe
 65                  70                  75                  80
Thr Phe Ser Glu Phe Leu Leu Lys Ser Val Ser Glu Leu Ala Ala Glu
             85                  90                  95
Phe Gly Leu Arg Ala Val Gly Pro Asn Ile Ala Leu Gly Arg Asn Lys
            100                 105                 110
Val Leu Met Arg Glu Arg Trp His Gln Ala Gly Ile Pro Gln Pro Ala
            115                 120                 125
Phe Arg Ala Val Arg Ser Glu Gln Glu Ile Ser Arg Val Ala Glu Leu
130                 135                 140
Asn Phe Pro Val Leu Val Lys Leu Ala Tyr Gly Ala Gly Ser Ile Gly
145                 150                 155                 160
Gln Gln Ile Val Asn Gly Met Asp Glu Leu Pro Ala Ala Ile Glu Arg
            165                 170                 175
Leu Ile Ala Ala Thr Glu Ala Ala Arg Arg Ala Gly Lys His Glu Phe
            180                 185                 190
Ser Glu His Glu Gly Phe Pro Gln Leu Ile Ala Glu Glu Ile Ile Gln
            195                 200                 205
Ser Thr Thr Thr Ser Trp Tyr Asp Glu Asp Gly Tyr Gly Asp Tyr Leu
            210                 215                 220
Ser Val Glu Gly Leu Val Arg Asp Gly Val Tyr Tyr Pro Leu Ala Met
225                 230                 235                 240
Thr Gly Arg Leu Arg Thr Ile Ala Pro Phe Thr Glu Leu Gly Asn Val
            245                 250                 255
Ala Pro Cys Val Leu Ser Thr Asp Lys Lys Ala Lys Ile Val Ala Leu
            260                 265                 270
Ile Lys Arg Ser Ile Asp Ala Leu Gly Phe Glu Asn Cys Ala Thr His
            275                 280                 285
Thr Glu Leu Lys Leu Met Ala Asp Gly Glu Val Ser Phe Leu Glu Thr
290                 295                 300
Ala Ala Arg Met Gly Gly Val Ala Ile Ala Lys Glu Leu Asp Glu Val
305                 310                 315                 320
Phe Gly Ile Asp Tyr Val Asp Leu Phe Leu Ser Val Ile Leu Gly Glu
            325                 330                 335
Pro Glu Thr Ile Pro Ala Phe Glu Gln Asn Ala Pro Arg Cys Ala Ala
            340                 345                 350
Ala Ser Val Ala Leu Ile Ala Cys Asp Ser Arg Gly Thr Pro Trp Gln
            355                 360                 365
Ser Thr Arg Gly Phe Ala Pro Glu Arg Val Asn Trp Gly Glu Leu Leu
            370                 375                 380
Asp Asp Met Ala Glu Val His Ile Gln Tyr Ala Gln Ser Ile Val Pro
385                 390                 395                 400
Gly Ser Pro Ile Ala Pro Tyr Asp Ile Ser Gly Leu Met Asn Tyr
            405                 410                 415
Ala Gly Gln Ala Phe Leu Val Ser Pro Thr Pro Ala Glu Leu Lys Arg
            420                 425                 430
```

```
Ala Ala Tyr Gln Leu Leu Asp Gly Leu Glu Gln Arg Leu Pro Leu His
            435                 440                 445

Gly

<210> SEQ ID NO 4
<211> LENGTH: 449
<212> TYPE: PRT
<213> ORGANISM: Ralstonia solanacearum MAFF211272

<400

```
Ala Ser Val Ala Leu Ile Ala Cys Asp Ser Arg Gly Thr Pro Trp Gln
            355                 360                 365

Ser Thr Arg Gly Phe Ala Pro Glu Arg Val Asn Trp Gly Glu Leu Leu
    370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Gly Leu Met Asn Tyr
                405                 410                 415

Ala Gly Gln Ala Phe Leu Val Ser Pro Thr Pro Ala Glu Leu Lys Arg
            420                 425                 430

Ala Ala Tyr Gln Leu Leu Asp Gly Leu Glu Gln Arg Leu Pro Leu His
        435                 440                 445

Ser

<210> SEQ ID NO 5
<211> LENGTH: 449
<212> TYPE: PRT
<213> ORGANISM: Ralstonia solanacearum MAFF211

```
Val Arg Gln Ala Ile Asp Ala Leu Gly Phe Glu Asn Cys Ala Thr His
        275                 280                 285
Thr Glu Leu Lys Leu Met Ala Asp Gly Glu Val Ser Phe Leu Glu Thr
    290                 295                 300
Ala Ala Arg Met Gly Gly Val Ala Ile Ala Lys Glu Leu Asp Glu Val
305                 310                 315                 320
Phe Gly Leu Asp Tyr Val Asp Leu Phe Leu Gly Val Ile Leu Gly Glu
                325                 330                 335
Pro Glu Ala Ile Pro Ala Phe Glu Gln Asn Ala Pro Arg Cys Ala Ala
            340                 345                 350
Ala Ser Val Ala Leu Ile Ala Cys Asp Ser Gln Gly Thr Pro Trp Lys
        355                 360                 365
Ser Thr Arg Gly Phe Ala Pro Glu Arg Val Asn Trp Gly Glu Leu Leu
    370                 375                 380
Asp Asp Met Ala Glu Val His Ile Gln Tyr Ala Gln Ser Ile Val Pro
385                 390                 395                 400
Gly Ser Pro Ile Ala Pro Tyr Asp Ile Ser Gly Gly Leu Met Asn Tyr
                405                 410                 415
Ala Gly Gln Ala Phe Leu Val Ser Pro Thr Pro Ala Lys Leu Lys Ser
            420                 425                 430
Ala Ala Tyr Gln Leu Leu Asp Gly Leu Glu Gln Arg Leu Pro Leu His
        435                 440                 445
Gly

<210> SEQ ID NO 6
<211> LENGTH: 449
<212> TYPE: PRT
<213> ORGANISM: Ralstonia solanacearum MAFF211403

<400> SEQUENCE: 6

Met Ser Lys Lys Ile Leu Tyr Val Tyr Ala Pro Ala Gly

```
Ser Glu His Glu Gly Phe Pro Gln Leu Ile Ala Glu Ile Ile Gln
            195                 200                 205

Ser Thr Ala Thr Ser Trp Tyr Asp Glu Asp Gly Tyr Gly Asp Tyr Leu
    210                 215                 220

Ser Val Glu Gly Leu Val Arg Asp Gly Val Tyr Tyr Pro Leu Ala Met
225                 230                 235                 240

Thr Gly Arg Leu Arg Thr Ile Ala Pro Phe Thr Glu Leu Gly Asn Val
                245                 250                 255

Ala Pro Cys Val Leu Ser Thr Asp Lys Lys Ala Lys Ile Val Ala Leu
            260                 265                 270

Ile Lys Arg Ser Ile Asp Ala Leu Gly Leu Glu Asn Cys Ala Thr His
    275                 280                 285

Thr Glu Leu Lys Leu Met Ala Asp Gly Glu Val Ser Phe Leu Glu Thr
290                 295                 300

Ala Ala Arg Met Gly Gly Val Ala Ile Ala Lys Glu Leu Asp Glu Val
305                 310                 315                 320

Phe Gly Ile Asp Tyr Val Asp Leu Phe Leu Ser Val Ile Leu Gly Glu
                325                 330                 335

Pro Glu Thr Ile Pro Ala Phe Glu Gln Asn Ala Pro Arg Cys Ala Ala
            340                 345                 350

Ala Ser Val Ala Leu Ile Ala Cys Asp Ser Arg Gly Thr Pro Trp Gln
    355                 360                 365

Ser Thr Arg Gly Phe Ala Pro Glu Arg Val Asn Trp Gly Glu Leu Leu
    370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Gly Leu Met Asn Tyr
                405                 410                 415

Ala Gly Gln Ala Phe Leu Val Ser Pro Thr Pro Ala Glu Leu Lys Arg
            420                 425                 430

Ala Ala Tyr Gln Leu Leu Asp Gly Leu Glu Gln Arg Leu Pro Leu His
    435                 440                 445

Ser

<210> SEQ ID NO 7
<211> LENGTH: 449
<212> TYPE: PRT
<213> ORGANISM: Ralstonia solanacearum MAFF211544

<400> SEQUENCE: 7

Met Ser Lys Lys Ile Leu Tyr Val Tyr Ala Pro Ala Gly Pro Pro Leu
1               5                   10                  15

Asp Tyr Cys Phe Pro Lys Ile Ala Arg Gly Glu Val His Thr Cys
                20                  25                  30

Ile Val Ser Pro Pro Ser Ala Ser Asn Met Glu Ile Leu Arg Arg His
        35                  40                  45

Ser Arg Ala Val His Asp Phe Ser His Val Ala Pro Ala Gln Ala Leu
    50                  55                  60

Glu Gln Val Arg Ala Leu Ala Gln Gln Ile Gly Pro Asp Ala Ile Phe
65                  70                  75                  80

Thr Phe Ser Glu Phe Leu Leu Lys Ser Val Ser Glu Leu Ala Ala Glu
                85                  90                  95

Phe Gly Leu Arg Ala Val Gly Pro Asn Ile Ala Leu Gly Arg Asn Lys
            100                 105                 110
```

Val Leu Met Arg Glu Arg Trp His Glu Ala Gly Ile Pro Gln Pro Ala
            115                 120                 125

Phe Arg Ala Val Arg Ser Glu Gln Glu Ile Ser Arg Val Ala Glu Leu
    130                 135                 140

Asn Phe Pro Val Leu Val Lys Leu Ala Tyr Gly Ala Gly Ser Ile Gly
145                 150                 155                 160

Gln Gln Ile Val Asn Gly Met Asp Glu Leu Pro Ala Ala Ile Glu Arg
                165                 170                 175

Leu Ile Ala Ala Thr Glu Ala Ala Arg Ala Gly Lys His Glu Phe
            180                 185                 190

Ser Glu His Glu Gly Phe Pro Gln Leu Ile Ala Glu Ile Ile Gln
    195                 200                 205

Ser Thr Thr Thr Ser Trp Tyr Asp Glu Asp Gly Tyr Gly Asp Tyr Leu
210                 215                 220

Ser Val Glu Gly Leu Val Arg Asp Gly Val Tyr Tyr Pro Leu Ala Met
225                 230                 235                 240

Thr Gly Arg Leu Arg Thr Ile Ala Pro Phe Thr Glu Leu Gly Asn Val
                245                 250                 255

Ala Pro Cys Val Leu Ser Thr Asp Lys Lys Ala Lys Ile Val Ala Leu
            260                 265                 270

Ile Lys Arg Ser Ile Asp Ala Leu Gly Phe Glu Asn Cys Ala Thr His
    275                 280                 285

Thr Glu Leu Lys Leu Met Ala Asp Gly Glu Val Ser Phe Leu Glu Thr
290                 295                 300

Ala Ala Arg Met Gly Gly Val Ala Ile Ala Lys Glu Leu Asp Glu Val
305                 310                 315                 320

Phe Gly Ile Asp Tyr Val Asp Leu Phe Leu Ser Val Ile Leu Gly Glu
                325                 330                 335

Pro Glu Thr Ile Pro Ala Phe Glu Gln Asn Ala Pro Arg Cys Ala Ala
            340                 345                 350

Ala Ser Val Ala Leu Ile Ala Cys Asp Ser Arg Gly Thr Pro Trp Gln
    355                 360                 365

Ser Thr Arg Gly Phe Ala Pro Glu Arg Val Asn Trp Gly Glu Leu Leu
370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Leu Met Asn Tyr
                405                 410                 415

Ala Gly Gln Ala Phe Leu Val Ser Pro Thr Pro Ala Glu Leu Lys Arg
            420                 425                 430

Ala Ala Tyr Gln Leu Leu Asp Gly Leu Glu Gln Arg Leu Pro Leu His
    435                 440                 445

Gly

<210> SEQ ID NO 8
<211> LENGTH: 449
<212> TYPE: PRT
<213> ORGANISM: Ralstonia solanacearum MAFF301520, Ralstonia
      solanacearum MAFF301523 and Ralstonia solanacearum MAFF301526

<400> SEQUENCE: 8

Met

-continued

```
Ile Val Ser Pro Pro Ser Ala Ser Asn Met Glu Ile Leu Arg Arg His
         35                  40                  45

Ser Arg Ala Val His Asp Phe Ser His Val Ala Pro Ala Gln Ala Leu
     50                  55                  60

Glu Gln Val Arg Ala Leu Ala Gln Gln Ile Gly Pro Asp Ala Ile Phe
 65              70                  75                  80

Thr Phe Ser Glu Phe Leu Leu Lys Ser Val Ser Glu Leu Ala Ala Gly
                 85                  90                  95

Phe Gly Leu Arg Ala Val Gly Pro Asn Ile Ala Leu Gly Arg Asn Lys
             100                 105                 110

Val Leu Met Arg Glu Arg Trp His Gln Ala Gly Ile Pro Gln Pro Ala
             115                 120                 125

Phe Arg Ala Val Arg Ser Glu Gln Glu Ile Ser Arg Val Ala Glu Leu
             130                 135                 140

Asn Phe Pro Val Leu Val Lys Leu Ala Tyr Gly Ala Gly Ser Ile Gly
145                 150                 155                 160

Gln Gln Ile Val Asn Gly Met Asp Glu Leu Pro Ala Ala Ile Glu Arg
             165                 170                 175

Leu Ile Ala Ala Thr Glu Ala Ala Arg Arg Ala Gly Lys His Glu Phe
             180                 185                 190

Ser Glu His Glu Gly Phe Pro Gln Leu Ile Ala Glu Glu Ile Ile Gln
             195                 200                 205

Ser Thr Thr Thr Ser Trp Tyr Asp Glu Asp Gly Tyr Gly Asp Tyr Leu
             210                 215                 220

Ser Val Glu Gly Leu Val Arg Asp Gly Val Tyr Tyr Pro Leu Ala Met
225                 230                 235                 240

Thr Gly Arg Leu Arg Thr Ile Ala Pro Phe Thr Glu Leu Gly Asn Val
             245                 250                 255

Ala Pro Cys Val Leu Ser Thr Asp Lys Lys Ala Lys Ile Val Ala Leu
             260                 265                 270

Ile Lys Arg Ser Ile Asp Ala Leu Gly Phe Glu Asn Cys Ala Thr His
             275                 280                 285

Thr Glu Leu Lys Leu Met Ala Asp Gly Glu Val Ser Phe Leu Glu Thr
             290                 295                 300

Ala Ala Arg Met Gly Gly Val Ala Ile Ala Lys Glu Leu Asp Glu Val
305                 310                 315                 320

Phe Gly Ile Asp Tyr Val Asp Leu Phe Leu Ser Val Ile Leu Gly Glu
             325                 330                 335

Pro Glu Thr Ile Pro Ala Phe Glu Gln Asn Ala Pro Arg Cys Ala Ala
             340                 345                 350

Ala Ser Val Ala Leu Ile Ala Cys Asp Ser Arg Gly Thr Pro Trp Gln
             355                 360                 365

Ser Thr Arg Gly Phe Ala Pro Glu Arg Val Asn Trp Gly Glu Leu Leu
             370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Gly Leu Met Asn Tyr
             405                 410                 415

Ala Gly Gln Ala Phe Leu Val Ser Pro Thr Pro Ala Glu Leu Lys Arg
             420                 425                 430

Ala Ala Tyr Gln Leu Leu Asp Gly Leu Glu Gln Arg Leu Pro Leu His
             435                 440                 445
```

Ser

<210> SEQ ID NO 9
<211> LENGTH: 449
<212> TYPE: PRT
<213> ORGANISM: Ralstonia solanacearum MAFF301522

<400> SEQUENCE: 9

Met Ser Lys Lys Ile Leu Tyr Val Tyr Ala Pro Ala Gly Pro Pro Leu
1               5                   10                  15

Asp Tyr Cys Phe Pro Lys Ile Ala Ala Arg Gly Glu Val His Thr Cys
            20                  25                  30

Ile Val Ser Pro Pro Ser Ala Ser Asn Met Glu Ile Leu Arg Arg His
        35                  40                  45

Ser Arg Ala Val His Asp Phe Ser His Val Ala Pro Ala Gln Ala Leu
    50                  55                  60

Glu Gln Val Arg Ala Leu Ala Gln Gln Ile Gly Pro Asp Ala Ile Phe
65                  70                  75                  80

Thr Phe Ser Glu Phe Leu Leu Lys Ser Val Ser Glu Leu Ala Ala Glu
                85                  90                  95

Phe Gly Leu Arg Ala Val Gly Pro Asn Ile Ala Leu Gly Arg Asn Lys
            100                 105                 110

Val Leu Met Arg Glu Arg Trp His Gln Ala Gly Ile Pro Gln Pro Ala
        115                 120                 125

Phe Arg Ala Val Arg Ser Glu Gln Glu Ile Ser Arg Val Ala Glu Leu
    130                 135                 140

Asn Phe Pro Val Leu Val Lys Leu Ala Tyr Gly Ala Gly Ser Ile Gly
145                 150                 155                 160

Gln Gln Ile Val Asn Gly Met Asp Glu Leu Pro Ala Ala Ile Glu Arg
                165                 170                 175

Leu Ile Ala Ala Thr Glu Ala Ala Arg Arg Ala Gly Lys His Glu Phe
            180                 185                 190

Ser Glu His Glu Gly Phe Pro Gln Leu Ile Ala Glu Glu Ile Ile Arg
        195                 200                 205

Ser Thr Thr Thr Ser Trp Tyr Asp Glu Asp Gly Tyr Gly Asp Tyr Leu
    210                 215                 220

Ser Val Glu Gly Leu Val Arg Asp Gly Val Tyr Tyr Pro Leu Ala Met
225                 230                 235                 240

Thr Gly Arg Leu Arg Thr Ile Ala Pro Phe Thr Glu Leu Gly Asn Val
                245                 250                 255

Ala Pro Cys Val Leu Ser Thr Asp Lys Lys Ala Lys Ile Val Ala Leu
            260                 265                 270

Ile Lys Arg Ser Ile Asp Ala Leu Gly Phe Glu Asn Cys Ala Thr His
        275                 280                 285

Thr Glu Leu Lys Leu Met Ala Asp Gly Glu Val Ser Phe Leu Glu Thr
    290                 295                 300

Ala Ala Arg Met Gly Gly Val Ala Ile Ala Lys Glu Leu Asp Glu Val
305                 310                 315                 320

Phe Gly Ile Asp Tyr Val Asp Leu Phe Leu Ser Val Ile Leu Gly Glu
                325                 330                 335

Pro Glu Thr Ile Pro Ala Phe Glu Gln Asn Ala Pro Arg Cys Ala Ala
            340                 345                 350

Ala Ser Val Ala Leu Ile Ala Cys Asp Ser Arg Gly Thr Pro Trp Gln
        355                 360                 365

-continued

```
Ser Thr Arg Gly Phe Ala Pro Glu Arg Val Asn Trp Gly Glu Leu Leu
    370                 375                 380

Asp Asp Met Ala Glu Val His Ile Gln Tyr Ala Gln Ser Ile Val Pro
385                 390                 395                 400

Gly Ser Pro Ile Ala Pro Tyr Asp Ile Ser Gly Gly Leu Met Asn Tyr
                405                 410                 415

Ala Gly Gln Ala Phe Leu Val Ser Pro Thr Pro Ala Glu Leu Lys Arg
            420                 425                 430

Ala Ala Tyr Gln Leu Leu Asp Gly Leu Glu Gln Arg Leu Pro Leu His
        435                 440                 445

Gly

<210> SEQ ID NO 10
<211> LENGTH: 1347
<212> TYPE: DNA
<213> ORGANISM: Ralstonia solanacearum MAFF301560

<400> SEQUENCE: 10 atg agc aag aag att ctg tac gtc tat gcg ccg gcc ggc ccg ccg ctg    48
Met Ser Lys Lys Ile Leu Tyr Val Tyr Ala Pro Ala Gly Pro Pro Leu
 1               5                  10                  15 gac tac tgt ttc ccg aaa atc gcc gcg cgc ggg gaa gtc cat acc tgc    96
Asp Tyr Cys Phe Pro Lys Ile Ala Ala Arg Gly Glu Val His Thr Cys
             20                  25                  30 atc gtc agc ccg ccg tcg gcc tcc aac atg gag atc ctg cgc cgg cac   144
Ile Val Ser Pro Pro Ser Ala Ser Asn Met Glu Ile Leu Arg Arg His
         35                  40                  45 agc cgt gcc gtg cat gac ttc agc cat gtc gcc ccg gcg cag gcg ctg   192
Ser Arg Ala Val His Asp Phe Ser His Val Ala Pro Ala Gln Ala Leu
     50                  55                  60 gag cag gtg cgc gcc ctg gcg cag cag atc ggc ccg gat gcg atc ttc   240
Glu Gln Val Arg Ala Leu Ala Gln Gln Ile Gly Pro Asp Ala Ile Phe
 65                  70                  75                  80 aca ttc tcc gag ttc ctg ctg aaa tcg gtc tcg gaa ctg gcg gcc gag   288
Thr Phe Ser Glu Phe Leu Leu Lys Ser Val Ser Glu Leu Ala Ala Glu
                 85                  90                  95 ttc ggg ctg cgc gcg gtc ggc ccc aat atc gcg ctc ggg cgc aac aag   336
Phe Gly Leu Arg Ala Val Gly Pro Asn Ile Ala Leu Gly Arg Asn Lys
            100                 105                 110 gta ctg atg cgc gaa cgc tgg cac cag gcc ggc atc ccg cag ccg gca   384
Val Leu Met Arg Glu Arg Trp His Gln Ala Gly Ile Pro Gln Pro Ala
        115                 120                 125 ttt cgc gcg gtc cgc agc gag cag gaa atc tcg cgc gtg gcc gag ctg   432
Phe Arg Ala Val Arg Ser Glu Gln Glu Ile Ser Arg Val Ala Glu Leu
    130                 135                 140 aac ttt ccg gtg ctg gtc aag ctg gcc tac ggc gcc ggc tcg atc ggc   480
Asn Phe Pro Val Leu Val Lys Leu Ala Tyr Gly Ala Gly Ser Ile Gly
145                 150                 155                 160 cag cag atc gtg aac ggc atg gac gag ttg ccg gcg gca atc gag cgc   528
Gln Gln Ile Val Asn Gly Met Asp Glu Leu Pro Ala Ala Ile Glu Arg
                165                 170                 175 ctg att gcc gcc acg gag gcg gca cgc agg gcg ggc aag cac gag ttt   576
Leu Ile Ala Ala Thr Glu Ala Ala Arg Arg Ala Gly Lys His Glu Phe
            180                 185                 190 tcc gaa cac gag ggc ttt ccg cag ctg atc gcc gaa gag atc att cag   624
Ser Glu His Glu Gly Phe Pro Gln Leu Ile Ala Glu Glu Ile Ile Gln
        195                 200                 205 tcc acc acc acc tcg tgg tac gac gaa gac ggc tac ggc gac tac ctg   672
Ser Thr Thr Thr Ser Trp Tyr Asp Glu Asp Gly Tyr Gly Asp Tyr Leu
```

```
agc gtg gaa ggg ctg gtg cgc gac ggt gtg tac tac ccg ttg gcc atg      720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg      768
Thr Gly Arg Leu Arg Thr Ile Ala Pro Phe Thr Glu Leu Gly Asn Val
            245                 250                 255 gcg ccg tgc gtg ctg agc acg gac aag aag gca aag atc gtt gcg ctg      816
Ala Pro Cys Val Leu Ser Thr Asp Lys Lys Ala Lys Ile Val Ala Leu
        260                 265                 270 atc aag cgg tcg atc gat gcg ctt ggc ttc gag aac tgc gcc acc cac      864
Ile Lys Arg Ser Ile Asp Ala Leu Gly Phe Glu Asn Cys Ala Thr His
    275                 280                 285 acc gag ctc aag ctg atg gcg gac ggc gag gtg tcg ttc ctg gag acc      912
Thr Glu Leu Lys Leu Met Ala Asp Gly Glu Val Ser Phe Leu Glu Thr
290                 295                 300 gcc gcc cgc atg ggc ggc gtg gcg atc gcc aag gag ctg gac gaa gta      960
Ala Ala Arg Met Gly Gly Val Ala Ile Ala Lys Glu Leu Asp Glu Val
305                 310                 315                 320 ttc ggg atc gat tat gtc gat ctg ttt ctg agc gtg atc ctg ggc gag     1008
Phe Gly Ile Asp Tyr Val Asp Leu Phe Leu Ser Val Ile Leu Gly Glu
            325                 330                 335 ccg gag acg att ccg gca ttc gag cag aac gcg ccg cgc tgt gcc gcg     1056
Pro Glu Thr Ile Pro Ala Phe Glu Gln Asn Ala Pro Arg Cys Ala Ala
        340                 345                 350 gcc tcg gtg gca ctg atc gcc tgc gac agt cgc ggc acg ccg tgg cag     1104
Ala Ser Val Ala Leu Ile Ala Cys Asp Ser Arg Gly Thr Pro Trp Gln
    355                 360                 365 agc acg cgc ggt ttt gcg ccg gag cgc gtg aac tgg ggc gaa ttg ctg     1152
Ser Thr Arg Gly Phe Ala Pro Glu Arg Val Asn Trp Gly Glu Leu Leu
370                 375                 380 gac gac atg gcc gaa gtg cat atc cag tat gcg cag tcg atc gtg ccg     1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac     1248
Gly Ser Pro Ile Ala Pro Tyr Asp Ile Ser Gly Gly Leu Met Asn Tyr
            405                 410                 415 gcc ggc cag gca ttc ctg gta agc ccg acg ccg gcc gag ctc aag cgt     1296
Ala Gly Gln Ala Phe Leu Val Ser Pro Thr Pro Ala Glu Leu Lys Arg
        420                 425                 430 gct gcg tac cag ttg ctg gac ggc ctg gag cag cgt ttg ccg ctg cat     1344
Ala Ala Tyr Gln Leu Leu Asp Gly Leu Glu Gln Arg Leu Pro Leu His
    435                 440                 445 agc                                                                  1347
Ser

<210> SEQ ID NO 11
<211> LENGTH: 1347
<212> TYPE: DNA
<213> ORGANISM: Rastonia solanacearum ATCC11696

<400> SEQUENCE: 11 atg agc aag aag att ctg tac gtc tat gcg ccg gcc ggt ccg ccg ctg

-continued

```
                35                  40                  45
agc cat gcc gtg cat gac ttc agc cat ctc gcc ccg gtg cag gcg ctg       192
Ser His Ala Val His Asp Phe Ser His Leu Ala Pro Val Gln Ala Leu
     50                  55                  60 gag cag gtg cgc gcg ctg gcg cag cag atc ggt ccg gat gcg atc ttc       240
Glu Gln Val Arg Ala Leu Ala Gln Gln Ile Gly Pro Asp Ala Ile Phe
 65                  70                  75                  80 acg ttc tcc gag ttc ctg ctg aaa tcg gtc tcg gaa atg gcg gcc ggg       288
Thr Phe Ser Glu Phe Leu Leu Lys Ser Val Ser Glu Met Ala Ala Gly
                 85                  90                  95 ttc ggg ctg cgc acg gtc ggc ccc agc atc gag ctg ggg cgc aac aag       336
Phe Gly Leu Arg Thr Val Gly Pro Ser Ile Glu Leu Gly Arg Asn Lys
            100                 105                 110 gtg ctg atg cgt gaa cgc tgg cag cag gcc ggc atc ccg cag ccg gca       384
Val Leu Met Arg Glu Arg Trp Gln Gln Ala Gly Ile Pro Gln Pro Ala
        115                 120                 125 ttt cgc gcg atc cgc agc gag cag gaa gtc tcg cgc gtg gcc gag ctg       432
Phe Arg Ala Ile Arg Ser Glu Gln Glu Val Ser Arg Val Ala Glu Leu
    130                 135                 140 aac ttt ccg gtg ctg gtc aag ctg gct tac ggc gcc ggc tcg atc ggc       480
Asn Phe Pro Val Leu Val Lys Leu Ala Tyr Gly Ala Gly Ser Ile Gly
145                 150                 155                 160 cag cag atc gtc aac ggc atg gac gaa ctg ccg gcg gcc atc gcg cgc       528
Gln Gln Ile Val Asn Gly Met Asp Glu Leu Pro Ala Ala Ile Ala Arg
                165                 170                 175 ctg att gcc gct acc gag gcg gca cgc aag gcg ggc aag cac gag ttc       576
Leu Ile Ala Ala Thr Glu Ala Ala Arg Lys Ala Gly Lys His Glu Phe
            180                 185                 190 tcc gaa cac gag ggc ttt ccg caa ctg atc gcc gaa gag atc att cag       624
Ser Glu His Glu Gly Phe Pro Gln Leu Ile Ala Glu Glu Ile Ile Gln
        195                 200                 205 tcc acc acc gcc tcg tgg tac gac gaa gac ggc tac ggc gac tac ctg       672
Ser Thr Thr Ala Ser Trp Tyr Asp Glu Asp Gly Tyr Gly Asp Tyr Leu
    210                 215                 220 agc gtg gaa ggg ctg gtg cgc gac ggt gtg tac tac ccg ttg gcc atg       720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg       768
Thr Gly Arg Leu Arg Thr Ile Ala Pro Phe Thr Glu Leu Gly Asn Val
                245                 250                 255 gcg ccg tgc gtg ctg agc gcg gac aag aag gcg aag atc gtg gcg ctg       816
Ala Pro Cys Val Leu Ser Ala Asp Lys Lys Ala Lys Ile Val Ala Leu
            260                 265                 270 atc aag cgc gcg atc gat gcg ctg ggc ttc gag aac tgc gcc acc cac       864
Ile Lys Arg Ala Ile Asp Ala Leu Gly Phe Glu Asn Cys Ala Thr His
        275                 280                 285 acc gag ctc aag ctg atg gcg gac ggc gag gtg tcg ttc ctg gag acc       912
Thr Glu Leu Lys Leu Met Ala Asp Gly Glu Val Ser Phe Leu Glu Thr
    290                 295                 300 gcg gcc cgc atg ggc ggc gtg gcg atc gcc aag gag ctg gac gag gtg       960
Ala Ala Arg Met Gly Gly Val Ala Ile Ala Lys Glu Leu Asp Glu Val
305                 310                 315                 320 ttc ggg ctc gac tac gtc gac ctg ttc ctg ggc gtg att ctc ggt gag      1008
Phe Gly Leu Asp Tyr Val Asp Leu Phe Leu Gly Val Ile Leu Gly Glu
                325                 330                 335 ccg gag gcg att ccg gca ttc gag cag aac gcg ccg cgc tgc gca gcg      1056
Pro Glu Ala Ile Pro Ala Phe Glu Gln Asn Ala Pro Arg Cys Ala Ala
            340                 345                 350 gcc tcg gtg gca ctg atc gct tgc gac agc cca ggg acc ccg tgg aag      1104
```

-continued

```
                Ala Ser Val Ala Leu Ile Ala Cys Asp Ser Pro Gly Thr Pro Trp Lys
                                355                 360                 365 agc acg cgc ggc ttc gcg ccg gag cgg gtg aac tgg ggc gag ttg ctg             1152
Ser Thr Arg Gly Phe Ala Pro Glu Arg Val Asn Trp Gly Glu Leu Leu
        370                 375                 380 gac gac atg gcc gaa gtg cac atc cag tat gcg cag tcg atc gtg ccg             1200
Asp Asp Met Ala Glu Val His Ile Gln Tyr Ala Gln Ser Ile Val Pro
385                 390                 395                 400 ggc agc ccg atc gcg ccc tac gat att tcc gga ggc ttg atg aac tac             1248
Gly Ser Pro Ile Ala Pro Tyr Asp Ile Ser Gly Gly Leu Met Asn Tyr
                405                 410                 415 gcc ggc cag gtc ttc ctg gtg agc ccc acg ccg gcc aag ctc aag cgt             1296
Ala Gly Gln Val Phe Leu Val Ser Pro Thr Pro Ala Lys Leu Lys Arg
            420                 425                 430 gct gcg tac cag ttg ctg gat ggc ctg gag cag cgt ttg ccg ctg cat             1344
Ala Ala Tyr Gln Leu Leu Asp Gly Leu Glu Gln Arg Leu Pro Leu His
        435                 440                 445 agc                                                                         1347
Ser <210> SEQ ID NO 12
<211> LENGTH: 1347
<212> TYPE: DNA
<213> ORGANISM: Ralstonia solanacearum MAFF211

```
                Leu Ile Ala Ala Thr Glu Ala Ala Arg Arg Ala Gly Lys His Glu Phe
                                180                 185                 190 tcc gaa cac gag ggc ttt ccg cag ctg atc gcc gaa gag atc att cag      624
Ser Glu His Glu Gly Phe Pro Gln Leu Ile Ala Glu Glu Ile Ile Gln
            195                 200                 205 tcc acc acc acc tcg tgg tac gac gaa gac ggc tac ggc gac tac ctg      672
Ser Thr Thr Thr Ser Trp Tyr Asp Glu Asp Gly Tyr Gly Asp Tyr Leu
    210                 215                 220 agc gtg gaa ggg ctg gtg cgc gac ggt gtg tac tac ccg ttg gcc atg      720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg      768
Thr Gly Arg Leu Arg Thr Ile Ala Pro Phe Thr Glu Leu Gly Asn Val
                245                 250                 255 gcg ccg tgc gtg ctg agc acg gac aag aag gca aag atc gtt gcg ctg      816
Ala Pro Cys Val Leu Ser Thr Asp Lys Lys Ala Lys Ile Val Ala Leu
            260                 265                 270 atc aag cgg tcg atc gat gcg ctt ggc ttc gag aac tgc gcc acc cac      864
Ile Lys Arg Ser Ile Asp Ala Leu Gly Phe Glu Asn Cys Ala Thr His
    275                 280                 285 acc gag ctc aag ctg atg gcg gac ggc gag gtg tcg ttc ctg gag acc      912
Thr Glu Leu Lys Leu Met Ala Asp Gly Glu Val Ser Phe Leu Glu Thr
290                 295                 300 gcc gcc cgc atg ggc ggc gtg gcg atc gcc aag gag ctg gac gaa gta      960
Ala Ala Arg Met Gly Gly Val Ala Ile Ala Lys Glu Leu Asp Glu Val
305                 310                 315                 320 ttc ggg atc gat tat gtc gat ctg ttt ctg agc gtg atc ctg ggc gag     1008
Phe Gly Ile Asp Tyr Val Asp Leu Phe Leu Ser Val Ile Leu Gly Glu
                325                 330                 335 ccg gag acg att ccg gca ttc gag cag aac gcg ccg cgc tgt gcc gcg     1056
Pro Glu Thr Ile Pro Ala Phe Glu Gln Asn Ala Pro Arg Cys Ala Ala
            340                 345                 350 gcc tcg gtg gca ctg atc gcc tgc gac agt cgc ggc acg ccg tgg cag     1104
Ala Ser Val Ala Leu Ile Ala Cys Asp Ser Arg Gly Thr Pro Trp Gln
    355                 360                 365 agc acg cgc ggt ttt gcg ccg gag cgc gtg aac tgg ggc gaa ttg ctg     1152
Ser Thr Arg Gly Phe Ala Pro Glu Arg Val Asn Trp Gly Glu Leu Leu
370                 375                 380 gac gac atg gcc gaa gtg cat atc cag tat gcg cag tcg atc gtg ccg     1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac     1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt     1296
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ttg cat     1344
Ala Ala Tyr Gln Leu Leu Asp Gly Leu Glu Gln Arg Leu Pro Leu His
    435                 440                 445 ggc                                                                 1347
Gly

<210> SEQ ID NO 13
<211> LENGTH: 1347
<212> TYPE: DNA
<213> ORGANISM: Ralstonia solanacearum MAFF211272

<400> SEQUENCE: 13 atg agc aag aag att ctg tac gtc tat gcg ccg gcc ggc ccg ccg ctg

```
Met Ser Lys Lys Ile Leu Tyr Val Tyr Ala Pro Ala Gly Pro Pro Leu
 1               5                  10                  15 gac tac tgt ttc ccg aaa atc gcc gcg cgc ggg gaa gtc cat acc tgt        96
Asp Tyr Cys Phe Pro Lys Ile Ala Ala Arg Gly Glu Val His Thr Cys
                20                  25                  30 atc gtc agc ccg ccg tcg gcc tcc aac atg gag atc ctg cgc cgg cac       144
Ile Val Ser Pro Pro Ser Ala Ser Asn Met Glu Ile Leu Arg Arg His
            35                  40                  45 agc cgt gcc gtg cat gac ttc agc cat gtc gcc ccg gcg cag gcg ctg       192
Ser Arg Ala Val His Asp Phe Ser His Val Ala Pro Ala Gln Ala Leu
        50                  55                  60 gag cag gtg cgc gcc ctg gcg cag cag atc ggc ccg gat gcg atc ttc       240
Glu Gln Val Arg Ala Leu Ala Gln Gln Ile Gly Pro Asp Ala Ile Phe
 65                 70                  75                  80 aca ttc tcc gag ttc ctg ctg aaa tcg gtc tcg gaa ctg gcg gcc ggg       288
Thr Phe Ser Glu Phe Leu Leu Lys Ser Val Ser Glu Leu Ala Ala Gly
                85                  90                  95 ttc ggg ctg cgc gcg gtc ggc ccc aat atc gcg ctc ggg cgc aac aag       336
Phe Gly Leu Arg Ala Val Gly Pro Asn Ile Ala Leu Gly Arg Asn Lys
            100                 105                 110 gta ctg atg cgc gaa cgc tgg cac cag gcc ggc atc ccg cag ccg gca       384
Val Leu Met Arg Glu Arg Trp His Gln Ala Gly Ile Pro Gln Pro Ala
        115                 120                 125 ttt cgc gcg gtc cgc agc gag cag gaa atc tcg cgc gtg gcc gag ctg       432
Phe Arg Ala Val Arg Ser Glu Gln Glu Ile Ser Arg Val Ala Glu Leu
    130                 135                 140 aac ttt ccg gtg ctg gtc aag ctg gcc tac ggc gcc ggc tcg atc ggc       480
Asn Phe Pro Val Leu Val Lys Leu Ala Tyr Gly Ala Gly Ser Ile Gly
145                 150                 155                 160 cag cag atc gtg aac ggc atg gac gag ttg ccg gcg gca atc gag cgc       528
Gln Gln Ile Val Asn Gly Met Asp Glu Leu Pro Ala Ala Ile Glu Arg
                165                 170                 175 ctg att gct gct acg gag gcg gca cgc agg gcg ggc aag cac gag ttt       576
Leu Ile Ala Ala Thr Glu Ala Ala Arg Arg Ala Gly Lys His Glu Phe
            180                 185                 190 tcc gaa cac gag ggc ttt ccg cag ctg atc gcc aaa gag atc att cag       624
Ser Glu His Glu Gly Phe Pro Gln Leu Ile Ala Lys Glu Ile Ile Gln
        195                 200                 205 tcc acc acc acc tcg tgg tac gac gaa gac ggc tac ggc gac tac ctg       672
Ser Thr Thr Thr Ser Trp Tyr Asp Glu Asp Gly Tyr Gly Asp Tyr Leu
    210                 215                 220 agc gtg gaa ggg ctg gtg cgc gac ggt gtg tac tac ccg ttg gcc atg       720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg       768
Thr Gly Arg Leu Arg Thr Ile Ala Pro Phe Thr Glu Leu Gly Asn Val
                245                 250                 255 gcg ccg tgc gtg ctg agc acg gac aag aag gca aag atc gtt gcg ctg       816
Ala Pro Cys Val Leu Ser Thr Asp Lys Lys Ala Lys Ile Val Ala Leu
            260                 265                 270 atc aag cgg tcg atc gat gcg ctt ggc ttc gag aac tgc gcc acc cac       864
Ile Lys Arg Ser Ile Asp Ala Leu Gly Phe Glu Asn Cys Ala Thr His
        275                 280                 285 acc gag ctc aag ctg atg gcg gac ggc gag gtg tcg ttc ctg gag acc       912
Thr Glu Leu Lys Leu Met Ala Asp Gly Glu Val Ser Phe Leu Glu Thr
    290                 295                 300 gcc gcc cgc atg ggc ggc gtg gcg atc gcc aag gag ctg gac gaa gta       960
Ala Ala Arg Met Gly Gly Val Ala Ile Ala Lys Glu Leu Asp Glu Val
305                 310                 315                 320
```

| | |
|---|---|
| ttc ggg atc gat tat gtc gat ctg ttt ctg agc gtg atc ctg ggc gag<br>Phe Gly Ile Asp Tyr Val Asp Leu Phe Leu Ser Val Ile Leu Gly Glu<br>325                        330                       335 | 1008 |
| ccg gag acg att ccg gca ttc gag cag aac gcg ccg cgc tgt gcc gcg<br>Pro Glu Thr Ile Pro Ala Phe Glu Gln Asn Ala Pro Arg Cys Ala Ala<br>340                        345                       350 | 1056 |
| gcc tcg gtg gca ctg atc gcc tgc gac agt cgc ggc acg ccg tgg cag<br>Ala Ser Val Ala Leu Ile Ala Cys Asp Ser Arg Gly Thr Pro Trp Gln<br>355                        360                       365 | 1104 |
| agc acg cgc ggt ttt gcg ccg gag cgc gtg aac tgg ggc gaa ttg ctg<br>Ser Thr Arg Gly Phe Ala Pro Glu Arg Val Asn Trp Gly Glu Leu Leu<br>370                        375                       380 | 1152 |
| gac gac atg gcc gaa gtg cat atc cag tat gcg cag tcg atc gtg ccg<br>Asp Asp Met Ala Glu Val His Ile Gln Tyr Ala Gln Ser Ile Val Pro<br>385                        390                       395                       400 | 1200 |
| ggc agc ccg atc gct ccc tac gac att tcc gga ggg ttg atg aac tac<br>Gly Ser Pro Ile Ala Pro Tyr Asp Ile Ser Gly Gly Leu Met Asn Tyr<br>405                        410                       415 | 1248 |
| gcc ggc cag gca ttc ctg gtc agc ccg acg ccg gcc gag ctc aag cgt<br>Ala Gly Gln Ala Phe Leu Val Ser Pro Thr Pro Ala Glu Leu Lys Arg<br>420                        425                       430 | 1296 |
| gct gcg tac cag ttg ctg gac ggc ctg gag cag cgt ttg ccg ttg cat<br>Ala Ala Tyr Gln Leu Leu Asp Gly Leu Glu Gln Arg Leu Pro Leu His<br>435                        440                       445 | 1344 |
| agc<br>Ser | 1347 |

<210> SEQ ID NO 14
<211> LENGTH: 1347
<212> TYPE: DNA
<213> ORGANISM: Ralstonia solanacearum MAFF211282 and Ralstonia
    solanacearum MAFF211396

<400> SEQUENCE: 14

| | |
|---

```
aac ttt ccg gtg ctg gtc aag ctg gcc tac ggc gcc ggc tcg atc ggc    480
Asn Phe Pro Val Leu Val Lys Leu Ala Tyr Gly Ala Gly Ser Ile Gly
145                 150                 155                 160 cag cag atc gtg aac ggc atg gac gag ctg ccg gcg gca atc gag cgc    528
Gln Gln Ile Val Asn Gly Met Asp Glu Leu Pro Ala Ala Ile Glu Arg
                165                 170                 175 ctg att gcc gct acg gag gcg gca cgc agg gcg ggc aag cac gag ttt    576
Leu Ile Ala Ala Thr Glu Ala Ala Arg Arg Ala Gly Lys His Glu Phe
        180                 185                 190 tcc gaa cac gag ggc ttt ccg cag ctg atc gcc gaa gag atc att cag    624
Ser Glu His Glu Gly Phe Pro Gln Leu Ile Ala Glu Glu Ile Ile Gln
    195                 200                 205 tcc acc acc acc tcg tgg tac gac gaa gac ggc tac ggc gac tac ctg    672
Ser Thr Thr Thr Ser Trp Tyr Asp Glu Asp Gly Tyr Gly Asp Tyr Leu
210                 215                 220 agc gtg gaa ggg ctg gtg cgc gac ggt gtg tac tac ccg ttg gcc atg    720
Ser Val Glu Gly Leu Val Arg Asp Gly Val Tyr Tyr Pro Leu Ala Met
225                 230                 235                 240 acc ggc cgg ctg cgc acc att gcg ccg ttc acc gaa ctc ggc aat gtg    768
Thr Gly Arg Leu Arg Thr Ile Ala Pro Phe Thr Glu Leu Gly Asn Val
                245                 250                 255 gcg ccg tgc gtg ctg agc acg gac aag aag gca aag atc gtt gcg ctg    816
Ala Pro Cys Val Leu Ser Thr Asp Lys Lys Ala Lys Ile Val Ala Leu
        260                 265                 270 atc aag cgg tcg atc gat gcg ctt ggc ttc gag aac tgc gcc acc cac    864
Ile Lys Arg Ser Ile Asp Ala Leu Gly Phe Glu Asn Cys Ala Thr His
    275                 280                 285 acc gag ctc aag ctg atg gcg gac ggc gag gtg tcg ttc ctg gag acc    912
Thr Glu Leu Lys Leu Met Ala Asp Gly Glu Val Ser Phe Leu Glu Thr
290                 295                 300 gcc gcc cgc atg ggc ggc gtg gcg atc gcc aag gag ctg gac gaa gta    960
Ala Ala Arg Met Gly Gly Val Ala Ile Ala Lys Glu Leu Asp Glu Val
305                 310                 315                 320 ttc ggg atc gat tat gtc gac ctg ttt ctg agc gtg atc ctg ggc gag   1008
Phe Gly Ile Asp Tyr Val Asp Leu Phe Leu Ser Val Ile Leu Gly Glu
                325                 330                 335 ccg gag acg att ccg gca ttc gag cag aac gcg ccg cgc tgt gcc gcg   1056
Pro Glu Thr Ile Pro Ala Phe Glu Gln Asn Ala Pro Arg Cys Ala Ala
        340                 345                 350 gcc tcg gtg gca ctg atc gcc tgc gac agt cgc ggc acg ccg tgg cag   1104
Ala Ser Val Ala Leu Ile Ala Cys Asp Ser Arg Gly Thr Pro Trp Gln
    355                 360                 365 agc acg cgc ggt ttt gcg ccg gag cgc gtg aac tgg ggc gaa ttg ctg   1152
Ser Thr Arg Gly Phe Ala Pro Glu Arg Val Asn Trp Gly Glu Leu Leu
370                 375                 380 gac gac atg gcc gaa gtg cat atc cag tat gcg cag tcg atc gtg ccg   1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac   1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt   1296
Ala Gly Gln Ala Phe Leu Val Ser Pro Thr Pro Ala Glu Leu Lys Arg
        420                 425                 430 gct gcg tac cag ttg ctg gac ggc ctg gag cag cgt ttg ccg ttg cat   1344
Ala Ala Tyr Gln Leu Leu Asp Gly Leu Glu Gln Arg Leu Pro Leu His
    435                 440                 445 ggc                                                                1347
Gly
```

<210> SEQ ID NO 15
<211> LENGTH: 1347
<212> TYPE: DNA
<213> ORGANISM: Ralstonia solanacearum MAFF211402

<400> SEQUENCE: 15

```
atg agc aag aag atc ctg tac gtc tac gcg ccg gcc ggc ccg ccg ctg      48
Met Ser Lys Lys Ile Leu Tyr Val Tyr Ala Pro Ala Gly Pro Pro Leu
  1               5                  10                  15 gat tac tgc ttc ccg aag atc gcc gcc cgc ggt gaa gtc cat acc tgc      96
Asp Tyr Cys Phe Pro Lys Ile Ala Ala Arg Gly Glu Val His Thr Cys
             20                  25                  30 atc gtc agc ccg ccg tcg gcc tcc aac atg gag atc ctg cgc cgc cac     144
Ile Val Ser Pro Pro Ser Ala Ser Asn Met Glu Ile Leu Arg Arg His
         35                  40                  45 agc cgc gcc gtg cac gac ttc agc cac gtc ggc ccg gtg cag gca ctg     192
Ser Arg Ala Val His Asp Phe Ser His Val Gly Pro Val Gln Ala Leu
     50                  55                  60 gcg cag gtg cgc gcc ctg gcg cag cag atc ggc ccg gac gtg atc ttc     240
Ala Gln Val Arg Ala Leu Ala Gln Gln Ile Gly Pro Asp Val Ile Phe
 65                  70                  75                  80 acg ttt tcc gag ttc ctg ctg aaa tcg gtc tcg gaa atg gcg gcc gat     288
Thr Phe Ser Glu Phe Leu Leu Lys Ser Val Ser Glu Met Ala Ala Asp
                 85                  90                  95 ttc ggg ctt cgc acc gtc ggc ccc aat atc gcg ctc gga cgc aac aag     336
Phe Gly Leu Arg Thr Val Gly Pro Asn Ile Ala Leu Gly Arg Asn Lys
            100                 105                 110 gtg ctg atg cgc gag cgc tgg cag cag gcc ggc atc ccg cag ccg gca     384
Val Leu Met Arg Glu Arg Trp Gln Gln Ala Gly Ile Pro Gln Pro Ala
        115                 120                 125 ttt cgc gcg atc cgc aac gag cag gaa gtc tcg cgc gtg gcc gag ctg     432
Phe Arg Ala Ile Arg Asn Glu Gln Glu Val Ser Arg Val Ala Glu Leu
    130                 135                 140 cac ttc ccg gtg ctg gtc aag ctg gcc tac ggt gcc ggc tcg atc ggt     480
His Phe Pro Val Leu Val Lys Leu Ala Tyr Gly Ala Gly Ser Ile Gly
145                 150                 155                 160 cag cag atc gtc aac ggc atg gac gaa ctg ccg acg gcg atc gcg cgc     528
Gln Gln Ile Val Asn Gly Met Asp Glu Leu Pro Thr Ala Ile Ala Arg
                165                 170                 175 ttg atc gcc gcc acc gag gcg gca cgc agg gcg ggc aag cac gag ttt     576
Leu Ile Ala Ala Thr Glu Ala Ala Arg Arg Ala Gly Lys His Glu Phe
            180                 185                 190 tcc gaa cac gag ggc ttt ccg caa ctg atc gcc gaa gag atc atc cag     624
Ser Glu His Glu Gly Phe Pro Gln Leu Ile Ala Glu Glu Ile Ile Gln
        195                 200                 205 tcc acc acc acc tcg tgg tac gac gaa gac ggc tac ggc gac tac ctg     672
Ser Thr Thr Thr Ser Trp Tyr Asp Glu Asp Gly Tyr Gly Asp Tyr Leu
    210                 215                 220 agc gtg gaa ggt ctg gtg cgc gac ggc gtg tac tac ccg ctg gcc atg     720
Ser Val Glu Gly Leu Val Arg Asp Gly Val Tyr Tyr Pro Leu Ala Met
225                 230                 235                 240 acc ggc cgg cta cgt acg att gcg ccg ttt acc gag cta ggc aat gtg     768
Thr Gly Arg Leu Arg Thr Ile Ala Pro Phe Thr Glu Leu Gly Asn Val
                245                 250                 255 gcg ccg tgc gtg ctg agc gag gac aag aag gcg aag atc gtt gcg ctg     816
Ala Pro Cys Val Leu Ser Glu Asp Lys Lys Ala Lys Ile Val Ala Leu
            260                 265                 270 gtc agg cag gcg atc gat gcg ctg ggc ttc gag aac tgc gcg acc cac     864
Val Arg Gln Ala Ile Asp Ala Leu Gly Phe Glu Asn Cys Ala Thr His
```

```
                275                 280                 285
acc gag ctc aag ctg atg gcg gac ggc gag gtg tcg ttc ctg gag acc    912
Thr Glu Leu Lys Leu Met Ala Asp Gly Glu Val Ser Phe Leu Glu Thr
    290                 295                 300 gcg gcc cgc atg ggc ggc gtg gcg atc gcc aag gag ctg gac gag gtg    960
Ala Ala Arg Met Gly Gly Val Ala Ile Ala Lys Glu Leu Asp Glu Val
305                 310                 315                 320 ttc ggg ctc gac tat gtc gac ctg ttc ctg ggc gtg att ctc ggc gag   1008
Phe Gly Leu Asp Tyr Val Asp Leu Phe Leu Gly Val Ile Leu Gly Glu
                325                 330                 335 ccg gag gcg att ccg gca ttc gag cag aat gcg ccg cgc tgc gcc gcg   1056
Pro Glu Ala Ile Pro Ala Phe Glu Gln Asn Ala Pro Arg Cys Ala Ala
            340                 345                 350 gcg tcg gtg gca ctg atc gct tgc gac agc caa ggc acg ccg tgg aag   1104
Ala Ser Val Ala Leu Ile Ala Cys Asp Ser Gln Gly Thr Pro Trp Lys
        355                 360                 365 agc acg cgc ggc ttt gcg ccg gag cgc gtg aac tgg ggc gag ttg ctg   1152
Ser Thr Arg Gly Phe Ala Pro Glu Arg Val Asn Trp Gly Glu Leu Leu
    370                 375                 380 gac gac atg gcc gaa gtg cat atc cag tat gcg cag tcg atc gtg ccg   1200
Asp Asp Met Ala Glu Val His Ile Gln Tyr Ala Gln Ser Ile Val Pro
385                 390                 395                 400 ggc agc ccg atc gcg ccc tat gac att tct ggg gga ttg atg aac tac   1248
Gly Ser Pro Ile Ala Pro Tyr Asp Ile Ser Gly Gly Leu Met Asn Tyr
                405                 410                 415 gcc ggc cag gca ttc ctg gtc agc ccg acg ccg gcc aag ctc aag agc   1296
Ala Gly Gln Ala Phe Leu Val Ser Pro Thr Pro Ala Lys Leu Lys Ser
            420                 425                 430 gct gca tac cag ttg ctg gat ggc ctt gag cag cgt ctg ccg ctg cac   1344
Ala Ala Tyr Gln Leu Leu Asp Gly Leu Glu Gln Arg Leu Pro Leu His
        435                 440                 445 ggc                                                                1347
Gly

<210> SEQ ID NO 16
<211> LENGTH: 1347
<212> TYPE: DNA
<213> ORGANISM: Ralstonia solanacearum MAFF211403

<400> SEQUENCE: 16 atg agc aag aag att ctg tac gtc tat gcg ccg gcc ggc ccg ccg ctg     48
Met Ser Lys Lys Ile Leu Tyr Val Tyr Ala Pro Ala Gly Pro Pro Leu
1               5                   10                  15 gac tac tgt ttc ccg aaa atc gcc gcg cgc ggg gaa gtc cat acc tgc     96
Asp Tyr Cys Phe Pro Lys Ile Ala Ala Arg Gly Glu Val His Thr Cys

|     |     |     |     |     |     |     |     |     |     |     |     |     |     |     |     | |
|---|---|---|---|---|---|---|---|---|---|---|---|---|---|---|---|---|
| | | 100 | | | | | 105 | | | | | 110 | | | | |
| gtg | ctg | atg | cgc | gaa | cgc | tgg | cac | cag | gcc | ggt | atc | ccg | cag | ccg | gca | 384 |
| Val | Leu | Met | Arg | Glu | Arg | Trp | His | Gln | Ala | Gly | Ile | Pro | Gln | Pro | Ala | |
| | | 115 | | | | | 120 | | | | | 125 | | | | |
| ttt | cgc | gcg | gtc | cgc | agc | gag | cag | gaa | atc | tcg | cgc | gtg | gcc | gag | ctg | 432 |
| Phe | Arg | Ala | Val | Arg | Ser | Glu | Gln | Glu | Ile | Ser | Arg | Val | Ala | Glu | Leu | |
| | 130 | | | | | 135 | | | | | 140 | | | | | |
| aac | ttt | ccg | gtg | ctg | gtc | aag | ctg | gcc | tac | ggc | gcc | ggc | tcg | atc | ggc | 480 |
| Asn | Phe | Pro | Val | Leu | Val | Lys | Leu | Ala | Tyr | Gly | Ala | Gly | Ser | Ile | Gly | |
| 145 | | | | | 150 | | | | | 155 | | | | | 160 | |
| cag | cag | atc | gtg | aac | ggc | atg | gac | gag | ttg | ccg | gcg | gca | atc | gag | cgc | 528 |
| Gln | Gln | Ile | Val | Asn | Gly | Met | Asp | Glu | Leu | Pro | Ala | Ala | Ile | Glu | Arg | |
| | | | | 165 | | | | | 170 | | | | | 175 | | |
| ctg | att | gcc | gcc | acg | gag | gcg | gca | cgc | agg | gcg | ggc | aag | cac | gag | ttt | 576 |
| Leu | Ile | Ala | Ala | Thr | Glu | Ala | Ala | Arg | Arg | Ala | Gly | Lys | His | Glu | Phe | |
| | | | 180 | | | | | 185 | | | | | 190 | | | |
| tcc | gaa | cac | gag | ggc | ttt | ccg | cag | ctg | atc | gcc | gaa | gag | atc | att | cag | 624 |
| Ser | Glu | His | Glu | Gly | Phe | Pro | Gln | Leu | Ile | Ala | Glu | Glu | Ile | Ile | Gln | |
| | | 195 | | | | | 200 | | | | | 205 | | | | |
| tcc | acc | gcc | acc | tcg | tgg | tac | gac | gaa | gac | ggc | tac | ggc | gac | tac | ctg | 672 |
| Ser | Thr | Ala | Thr | Ser | Trp | Tyr | Asp | Glu | Asp | Gly | Tyr | Gly | Asp | Tyr | Leu | |
| | 210 | | | | | 215 | | | | | 220 | | | | | |
| agc | gtg | gaa | ggg | ctg | gtg | cgc | gac | ggt | gtg | tac | tac | ccg | ttg | gcc | atg | 720 |
| Ser | Val | Glu | Gly | Leu | Val | Arg | Asp | Gly | Val | Tyr | Tyr | Pro | Leu | Ala | Met | |
| 225 | | | | | 230 | | | | | 235 | | | | | 240 | |
| acc | ggc | cgg | ctg | cgc | acc | att | gcg | ccg | ttt | acc | gaa | ctc | ggc | aat | gtg | 768 |
| Thr | Gly | Arg | Leu | Arg | Thr | Ile | Ala | Pro | Phe | Thr | Glu | Leu | Gly | Asn | Val | |
| | | | | 245 | | | | | 250 | | | | | 255 | | |
| gcg | ccg | tgc | gtg | ctg | agc | acg | gac | aag | aag | gca | aag | atc | gtt | gcg | ctg | 816 |
| Ala | Pro | Cys | Val | Leu | Ser | Thr | Asp | Lys | Lys | Ala | Lys | Ile | Val | Ala | Leu | |
| | | | 260 | | | | | 265 | | | | | 270 | | | |
| atc | aag | cgg | tcg | atc | gat | gcg | ctt | ggc | ctc | gag | aac | tgc | gcc | acc | cac | 864 |
| Ile | Lys | Arg | Ser | Ile | Asp | Ala | Leu | Gly | Leu | Glu | Asn | Cys | Ala | Thr | His | |
| | | 275 | | | | | 280 | | | | | 285 | | | | |
| acc | gag | ctc | aag | ctg | atg | gcg | gac | ggc | gag | gtg | tcg | ttc | ctg | gag | acc | 912 |
| Thr | Glu | Leu | Lys | Leu | Met | Ala | Asp | Gly | Glu | Val | Ser | Phe | Leu | Glu | Thr | |
| | 290 | | | | | 295 | | | | | 300 | | | | | |
| gcc | gcc | cgc | atg | ggc | ggc | gtg | gcg | atc | gcc | aag | gag | ctg | gac | gaa | gta | 960 |
| Ala | Ala | Arg | Met | Gly | Gly | Val | Ala | Ile | Ala | Lys | Glu | Leu | Asp | Glu | Val | |
| 305 | | | | | 310 | | | | | 315 | | | | | 320 | |
| ttc | ggg | atc | gat | tat | gtc | gac | ctg | ttt | ctg | agc | gtg | atc | ctg | ggc | gag | 1008 |
| Phe | Gly | Ile | Asp | Tyr | Val | Asp | Leu | Phe | Leu | Ser | Val | Ile | Leu | Gly | Glu | |
| | | | | 325 | | | | | 330 | | | | | 335 | | |
| ccg | gag | acg | att | ccg | gca | ttc | gag | cag | aac | gcg | ccg | cgc | tgt | gcc | gcg | 1056 |
| Pro | Glu | Thr | Ile | Pro | Ala | Phe | Glu | Gln | Asn | Ala | Pro | Arg | Cys | Ala | Ala | |
| | | | 340 | | | | | 345 | | | | | 350 | | | |
| gcc | tcg | gtg | gca | ctg | atc | gcc | tgc | gac | agt | cgc | ggc | acg | ccg | tgg | cag | 1104 |
| Ala | Ser | Val | Ala | Leu | Ile | Ala | Cys | Asp | Ser | Arg | Gly | Thr | Pro | Trp | Gln | |
| | | 355 | | | | | 360 | | | | | 365 | | | | |
| agc | acg | cgc | ggt | ttt | gcg | ccg | gag | cgc | gtg | aac | tgg | ggc | gaa | ttg | ctg | 1152 |
| Ser | Thr | Arg | Gly | Phe | Ala | Pro | Glu | Arg | Val | Asn | Trp | Gly | Glu | Leu | Leu | |
| | 370 | | | | | 375 | | | | | 380 | | | | | |
| gac | gac | atg | gcc | gaa | gtg | cat | atc | cag | tat | gcg | cag | tcg | atc | gtg | ccg | 1200 |
| Asp | Asp | Met | Ala | Glu | Val | His | Ile | Gln | Tyr | Ala | Gln | Ser | Ile | Val | Pro | |
| 385 | | | | | 390 | | | | | 395 | | | | | 400 | |
| ggc | agc | ccg | atc | gct | ccc | tac | gac | att | tcc | gga | ggg | ttg | atg | aac | tac | 1248 |
| Gly | Ser | Pro | Ile | Ala | Pro | Tyr | Asp | Ile | Ser | Gly | Gly | Leu | Met | Asn | Tyr | |
| | | | | 405 | | | | | 410 | | | | | 415 | | |
| gcc | ggc | cag | gca | ttc | ctg | gta | agc | ccg | acg | ccg | gcc | gag | ctc | aag | cgt | 1296 |

```
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ttg cat    1344
Ala Ala Tyr Gln Leu Leu Asp Gly Leu Glu Gln Arg Leu Pro Leu His
            435                 440                 445 agc                                                                 1347
Ser

<210> SEQ ID NO 17
<211> LENGTH: 1347
<212> TYPE: DNA
<213> ORGANISM: Ralstonia solanacearum MAFF211544

<400> SEQUENCE:

-continued

```
                Thr Gly Arg Leu Arg Thr Ile Ala Pro Phe Thr Glu Leu Gly Asn Val
                                245                 250                 255 gcg ccg tgc gtg ctg agc acg gac aag aag gca aag atc gtt gcg ctg       816
Ala Pro Cys Val Leu Ser Thr Asp Lys Lys Ala Lys Ile Val Ala Leu
            260                 265                 270 atc aag cgg tcg atc gat gcg ctt ggc ttc gag aac tgc gcc acc cac       864
Ile Lys Arg Ser Ile Asp Ala Leu Gly Phe Glu Asn Cys Ala Thr His
275                 280                 285 acc gag ctc aag ctg atg gcg gac ggc gag gtg tcg ttc ctg gag acc       912
Thr Glu Leu Lys Leu Met Ala Asp Gly Glu Val Ser Phe Leu Glu Thr
        290                 295                 300 gcc gcc cgc atg ggc ggc gtg gcg atc gcc aag gag ctg gac gaa gta       960
Ala Ala Arg Met Gly Gly Val Ala Ile Ala Lys Glu Leu Asp Glu Val
305                 310                 315                 320 ttc ggg atc gat tat gtc gat ctg ttt ctg agc gtg atc ctg ggc gag      1008
Phe Gly Ile Asp Tyr Val Asp Leu Phe Leu Ser Val Ile Leu Gly Glu
                325                 330                 335 ccg gag acg att ccg gca ttc gag cag aac gcg ccg cgc tgt gcc gcg      1056
Pro Glu Thr Ile Pro Ala Phe Glu Gln Asn Ala Pro Arg Cys Ala Ala
            340                 345                 350 gcc tcg gtg gca ctg atc gcc tgc gac agt cgc ggc acg ccg tgg cag      1104
Ala Ser Val Ala Leu Ile Ala Cys Asp Ser Arg Gly Thr Pro Trp Gln
355                 360                 365 agc acg cgc ggt ttt gcg ccg gag cgc gtg aac tgg ggc gaa ttg ctg      1152
Ser Thr Arg Gly Phe Ala Pro Glu Arg Val Asn Trp Gly Glu Leu Leu
        370                 375                 380 gac gac atg gcc gaa gtg cat atc cag tat gcg cag tcg atc gtg ccg      1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac      1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt      1296
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ttg cat      1344
Ala Ala Tyr Gln Leu Leu Asp Gly Leu Glu Gln Arg Leu Pro Leu His
435                 440                 445 ggc                                                                   1347
Gly

<210> SEQ ID NO 18
<211> LENGTH: 1347
<212> TYPE: DNA
<213> ORGANISM: Ralstonia solanacearum MAFF301520

<400

-continued

```
             Glu Gln Val Arg Ala Leu Ala Gln Gln Ile Gly Pro Asp Ala Ile Phe
             65                  70                  75                  80 aca ttc tcc gag ttc ctg ctg aaa tcg gtc tcg gaa ctg gcg gcc ggg            288
Thr Phe Ser Glu Phe Leu Leu Lys Ser Val Ser Glu Leu Ala Ala Gly
                    85                  90                  95 ttc ggg ctg cgc gcg gtc ggc ccc aat atc gcg ctc ggg cgc aac aag            336
Phe Gly Leu Arg Ala Val Gly Pro Asn Ile Ala Leu Gly Arg Asn Lys
            100                 105                 110 gtg ctg atg cgc gaa cgc tgg cac cag gcc ggt atc ccg cag ccg gca            384
Val Leu Met Arg Glu Arg Trp His Gln Ala Gly Ile Pro Gln Pro Ala
        115                 120                 125 ttt cgc gcg gtc cgc agc gag cag gaa atc tcg cgc gtg gcc gag ctg            432
Phe Arg Ala Val Arg Ser Glu Gln Glu Ile Ser Arg Val Ala Glu Leu
    130                 135                 140 aac ttt ccg gtg ctg gtc aag ctg gcc tac ggc gcc ggc tcg atc ggc            480
Asn Phe Pro Val Leu Val Lys Leu Ala Tyr Gly Ala Gly Ser Ile Gly
145                 150                 155                 160 cag cag atc gtg aac ggc atg gac gag ttg ccg gcg gca atc gag cgc            528
Gln Gln Ile Val Asn Gly Met Asp Glu Leu Pro Ala Ala Ile Glu Arg
                165                 170                 175 ctg att gcc gcc acg gag gcg gca cgc agg gcg ggc aag cac gag ttt            576
Leu Ile Ala Ala Thr Glu Ala Ala Arg Arg Ala Gly Lys His Glu Phe
            180                 185                 190 tcc gaa cac gag ggc ttt ccg cag ctg atc gcc gaa gag atc att cag            624
Ser Glu His Glu Gly Phe Pro Gln Leu Ile Ala Glu Glu Ile Ile Gln
        195                 200                 205 tcc acc acc acc tcg tgg tac gac gaa gac ggc tac ggc gac tac ctg            672
Ser Thr Thr Thr Ser Trp Tyr Asp Glu Asp Gly Tyr Gly Asp Tyr Leu
    210                 215                 220 agc gtg gaa ggg ctg gtg cgc gac ggt gtg tac tac ccg ttg gcc atg            720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg            768
Thr Gly Arg Leu Arg Thr Ile Ala Pro Phe Thr Glu Leu Gly Asn Val
                245                 250                 255 gcg ccg tgc gtg ctg agc acg gac aag aag gca aag atc gtt gcg ctg            816
Ala Pro Cys Val Leu Ser Thr Asp Lys Lys Ala Lys Ile Val Ala Leu
            260                 265                 270 atc aag cgg tcg atc gat gcg ctt ggc ttc gag aac tgc gcc acc cac            864
Ile Lys Arg Ser Ile Asp Ala Leu Gly Phe Glu Asn Cys Ala Thr His
        275                 280                 285 acc gag ctc aag ctg atg gcg gac ggc gag gtg tcg ttc ctg gag acc            912
Thr Glu Leu Lys Leu Met Ala Asp Gly Glu Val Ser Phe Leu Glu Thr
    290                 295                 300 gcc gcc cgc atg ggc ggc gtg gcg atc gcc aag gag ctg gac gaa gta            960
Ala Ala Arg Met Gly Gly Val Ala Ile Ala Lys Glu Leu Asp Glu Val
305                 310                 315                 320 ttc ggg atc gat tat gtc gac ctg ttt ctg agc gtg atc ctg ggc gag           1008
Phe Gly Ile Asp Tyr Val Asp Leu Phe Leu Ser Val Ile Leu Gly Glu
                325                 330                 335 ccg gag acg att ccg gca ttc gag cag aac gcg ccg cgc tgt gcc gcg           1056
Pro Glu Thr Ile Pro Ala Phe Glu Gln Asn Ala Pro Arg Cys Ala Ala
            340                 345                 350 gcc tcg gtg gca ctg atc gcc tgc gac agt cgc ggc acg ccg tgg cag           1104
Ala Ser Val Ala Leu Ile Ala Cys Asp Ser Arg Gly Thr Pro Trp Gln
        355                 360                 365 agc acg cgc ggt ttt gcg ccg gag cgc gtg aac tgg ggc gaa ttg ctg           1152
Ser Thr Arg Gly Phe Ala Pro Glu Arg Val Asn Trp Gly Glu Leu Leu
    370                 375                 380
```

```
gac gac atg gcc gaa gtg cat atc cag tat gcg cag tcg atc gtg ccg      1200
Asp Asp Met Ala Glu Val His Ile Gln Tyr Ala Gln Ser Ile Val Pro
385             390                 395                 400 ggc agc ccg atc gct ccc tac gac att tcc gga ggg ttg atg aac tac      1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt      1296
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ttg cat      1344
Ala Ala Tyr Gln Leu Leu Asp Gly Leu Glu Gln Arg Leu Pro Leu His
        435                 440                 445 agc                                                                   1347
Ser

<210> SEQ ID NO 19
<211> LENGTH: 1347
<212> TYPE: DNA
<213> ORGANISM: Ralstonia solanacearum MAFF301522

<400> SEQUENCE: 19 atg agc aag aag att ctg tac gtc tat gcg ccg gcc ggc ccg ccg ctg       48
Met Ser Lys Lys Ile Leu Tyr Val Tyr Ala Pro Ala Gly Pro Pro Leu
1               5                   10                  15 gac tac tgt ttc ccg aaa atc gcc gcg cgc ggg gaa gtc cat acc tgt       96
Asp Tyr Cys Phe Pro Lys Ile Ala Ala Arg Gly Glu Val His Thr Cys
                20                  25                  30 atc gtc agc ccg ccg tcg gcc tcc aac atg gag atc ctg cgc cgg cac      144
Ile Val Ser Pro Pro Ser Ala Ser Asn Met Glu Ile Leu Arg Arg His
            35                  40                  45 agc cgt gcc gtg cat gac ttc agc cat gtc gcc ccg gcg cag gcg ctg      192
Ser Arg Ala Val His Asp Phe Ser His Val Ala Pro Ala Gln Ala Leu
        50                  55                  60 gag cag gtg cgc gcc ctg gcg cag cag atc ggc ccg gat gcg atc ttc      240
Glu Gln Val Arg Ala Leu Ala Gln Gln Ile Gly Pro Asp Ala Ile Phe
65                  70                  75                  80 aca ttc tcc gag ttc ctg ctg aaa tcg gtc tcg gaa ctg gcg gcc gag      288
Thr Phe Ser Glu Phe Leu Leu Lys Ser Val Ser Glu Leu Ala Ala Glu
                85                  90                  95 ttc ggg ctg cgc gcg gtc ggc ccc aat atc gcg ctc ggg cgc aac aag      336
Phe Gly Leu Arg Ala Val Gly Pro Asn Ile Ala Leu Gly Arg Asn Lys
                100                 105                 110 gta ctg atg cgc gaa cgc tgg cac cag gcc ggc atc ccg cag ccg gca      384
Val Leu Met Arg Glu Arg Trp His Gln Ala Gly Ile Pro Gln Pro Ala
            115                 120                 125 ttt cgc gcg gtc cgc agc gag cag gaa atc tcg cgc gtg gcc gag ctg      432
Phe Arg Ala Val Arg Ser Glu Gln Glu Ile Ser Arg Val Ala Glu Leu
        130                 135                 140 aac ttt ccg gtg ctg gtc aag ctg gcc tac ggc gcc ggc tcg atc ggc      480
Asn Phe Pro Val Leu Val Lys Leu Ala Tyr Gly Ala Gly Ser Ile Gly
145                 150                 155                 160 cag cag atc gtg aac ggc atg gac gag ctg ccg gcg gca atc gag cgc      528
Gln Gln Ile Val Asn Gly Met Asp Glu Leu Pro Ala Ala Ile Glu Arg
                165                 170                 175 ctg att gcc gct acg gag gcg gca cgc agg gcg ggc aag cac gag ttt      576
Leu Ile Ala Ala Thr Glu Ala Ala Arg Arg Ala Gly Lys His Glu Phe
                180                 185                 190 tcc gaa cac gag ggc ttt ccg cag ctg atc gcc gaa gag atc att cgg      624
Ser Glu His Glu Gly Phe Pro Gln Leu Ile Ala Glu Glu Ile Ile Arg
            195                 200                 205
```

```
                                  -continued tcc acc acc acc tcg tgg tac gac gaa gac ggc tac ggc gac tac ctg        672
Ser Thr Thr Thr Ser Trp Tyr Asp Glu Asp Gly Tyr Gly Asp Tyr Leu
    210                 215                 220 agc gtg gaa ggg ctg gtg cgc gac ggt gtg tac tac ccg ttg gcc atg        720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg        768
Thr Gly Arg Leu Arg Thr Ile Ala Pro Phe Thr Glu Leu Gly Asn Val
                245                 250                 255 gcg ccg tgc gtg ctg agc acg gac aag aag gca aag atc gtt gcg ctg        816
Ala Pro Cys Val Leu Ser Thr Asp Lys Lys Ala Lys Ile Val Ala Leu
            260                 265                 270 atc aag cgg tcg atc gat gcg ctt ggc ttc gag aac tgc gcc acc cac        864
Ile Lys Arg Ser Ile Asp Ala Leu Gly Phe Glu Asn Cys Ala Thr His
        275                 280                 285 acc gag ctc aag ctg atg gcg gac ggc gag gtg tcg ttc ctg gag acc        912
Thr Glu Leu Lys Leu Met Ala Asp Gly Glu Val Ser Phe Leu Glu Thr
    290                 295                 300 gcc gcc cgc atg ggc ggc gtg gcg atc gcc aag gag ctg gac gaa gta        960
Ala Ala Arg Met Gly Gly Val Ala Ile Ala Lys Glu Leu Asp Glu Val
305                 310                 315                 320 ttc ggg atc gat tat gtc gac ctg ttt ctg agc gtg atc ctg ggc gag       1008
Phe Gly Ile Asp Tyr Val Asp Leu Phe Leu Ser Val Ile Leu Gly Glu
                325                 330                 335 ccg gag acg att ccg gca ttc gag cag aac gcg ccg cgc tgt gcc gcg       1056
Pro Glu Thr Ile Pro Ala Phe Glu Gln Asn Ala Pro Arg Cys Ala Ala
            340                 345                 350 gcc tcg gtg gca ctg atc gcc tgc gac agt cgc ggc acg ccg tgg cag       1104
Ala Ser Val Ala Leu Ile Ala Cys Asp Ser Arg Gly Thr Pro Trp Gln
        355                 360                 365 agc acg cgc ggt ttt gcg ccg gag cgc gtg aac tgg ggc gaa ttg ctg       1152
Ser Thr Arg Gly Phe Ala Pro Glu Arg Val Asn Trp Gly Glu Leu Leu
    370                 375                 380 gac gac atg gcc gaa gtg cat atc cag tat gcg cag tcg atc gtg ccg       1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac       1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt       1296
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ttg cat       1344
Ala Ala Tyr Gln Leu Leu Asp Gly Leu Glu Gln Arg Leu Pro Leu His
        435                 440                 445 ggc                                                                   1347
Gly

<210> SEQ ID NO 20
<211> LENGTH: 1347
<212> TYPE: DNA
<213> ORGANISM: Ralstonia solanacearum MAFF301523

<400> SEQUENCE: 20 atg agc aag aag att ctg tac gtc tat gcg ccg gcc ggc ccg ccg ctg         48
Met Ser Lys Lys Ile Leu Tyr Val Tyr Ala Pro Ala Gly Pro Pro Leu
1               5                   10                  15 gac tac tgt ttc ccg aaa atc gcc gcg cgc ggg gaa gtc cat acc tgc         96
Asp Tyr Cys Phe Pro Lys Ile Ala Ala Arg Gly Glu Val His Thr Cys
                20                  25                  30
```

| | | |
|---|---|---|
| atc gtc agc ccg ccg tcg gcc tcc aac atg gag atc ctg cgc cgg cac<br>Ile Val Ser Pro Pro Ser Ala Ser Asn Met Glu Ile Leu Arg Arg His<br>35                  40                  45 | 144 |
| agc cgt gcc gtg cat gac ttc agc cat gtc gcc ccg gcg cag gcg ctg<br>Ser Arg Ala Val His Asp Phe Ser His Val Ala Pro Ala Gln Ala Leu<br>50                  55                  60 | 192 |
| gag cag gtg cgc gcc ctg gcg cag cag atc ggc ccg gat gcg atc ttc<br>Glu Gln Val Arg Ala Leu Ala Gln Gln Ile Gly Pro Asp Ala Ile Phe<br>65               70                75                80 | 240 |
| aca ttc tcc gag ttc ctg ctg aaa tcg gtc tcg gaa ctg gcg gcc ggg<br>Thr Phe Ser Glu Phe Leu Leu Lys Ser Val Ser Glu Leu Ala Ala Gly<br>                  85                  90                95 | 288 |
| ttc ggg ctg cgc gcg gtc ggc ccc aat atc gcg ctc ggg cgc aac aag<br>Phe Gly Leu Arg Ala Val Gly Pro Asn Ile Ala Leu Gly Arg Asn Lys<br>             100                105             110 | 336 |
| gtg ctg atg cgc gaa cgc tgg cac cag gcc ggt atc ccg cag ccg gca<br>Val Leu Met Arg Glu Arg Trp His Gln Ala Gly Ile Pro Gln Pro Ala<br>            115                120             125 | 384 |
| ttt cgc gcg gtc cgc agc gag cag gaa atc tcg cgc gtg gcc gag ctg<br>Phe Arg Ala Val Arg Ser Glu Gln Glu Ile Ser Arg Val Ala Glu Leu<br>130                  135                140 | 432 |
| aac ttt ccg gtg ctg gtc aag ctg gcc tac ggc gcc ggc tcg atc ggc<br>Asn Phe Pro Val Leu Val Lys Leu Ala Tyr Gly Ala Gly Ser Ile Gly<br>145                  150               155              160 | 480 |
| cag cag atc gtg aac ggc atg gac gag ttg ccg gcg gca atc gag cgc<br>Gln Gln Ile Val Asn Gly Met Asp Glu Leu Pro Ala Ala Ile Glu Arg<br>                   165             170              175 | 528 |
| ctg att gcc gcc acg gag gcg gca cgc agg gcg ggc aag cac gag ttt<br>Leu Ile Ala Ala Thr Glu Ala Ala Arg Arg Ala Gly Lys His Glu Phe<br>            180                185               190 | 576 |
| tcc gaa cac gag ggc ttc ccg cag ctg atc gcc gaa gag atc att cag<br>Ser Glu His Glu Gly Phe Pro Gln Leu Ile Ala Glu Glu Ile Ile Gln<br>               195              200             205 | 624 |
| tcc acc acc acc tcg tgg tac gac gaa gac ggc tac ggc gac tac ctg<br>Ser Thr Thr Thr Ser Trp Tyr Asp Glu Asp Gly Tyr Gly Asp Tyr Leu<br>210                  215                220 | 672 |
| agc gtg gaa ggg ctg gtg cgc gac ggt gtg tac tac ccg ttg gcc atg<br>Ser Val Glu Gly Leu Val Arg Asp Gly Val Tyr Tyr Pro Leu Ala Met<br>225                  230               235              240 | 720 |
| acc ggc cgg ctg cgc acc att gcg ccg ttt acc gaa ctc ggc aat gtg<br>Thr Gly Arg Leu Arg Thr Ile Ala Pro Phe Thr Glu Leu Gly Asn Val<br>                   245             250              255 | 768 |
| gcg ccg tgc gtg ctg agc acg gac aag aag gca aag atc gtt gcg ctg<br>Ala Pro Cys Val Leu Ser Thr Asp Lys Lys Ala Lys Ile Val Ala Leu<br>            260                265             270 | 816 |
| atc aag cgg tcg atc gat gcg ctt ggc ttc gag aac tgc gcc acc cac<br>Ile Lys Arg Ser Ile Asp Ala Leu Gly Phe Glu Asn Cys Ala Thr His<br>             275                280             285 | 864 |
| acc gag ctc aag ctg atg gcg gac ggc gag gtg tcg ttc ctg gag acc<br>Thr Glu Leu Lys Leu Met Ala Asp Gly Glu Val Ser Phe Leu Glu Thr<br>290                  295                300 | 912 |
| gcc gcc cgc atg ggc ggc gtg gcg atc gcc aag gag ctg gac gaa gta<br>Ala Ala Arg Met Gly Gly Val Ala Ile Ala Lys Glu Leu Asp Glu Val<br>305                  310               315              320 | 960 |
| ttc ggg atc gat tat gtc gac ctg ttt ctg agc gtg atc ctg ggc gag<br>Phe Gly Ile Asp Tyr Val Asp Leu Phe Leu Ser Val Ile Leu Gly Glu<br>                   325             330              335 | 1008 |
| ccg gag acg att ccg gca ttc gag cag aac gcg ccg cgc tgt gcc gcg<br>Pro Glu Thr Ile Pro Ala Phe Glu Gln Asn Ala Pro Arg Cys Ala Ala<br>            340                345             350 | 1056 |

-continued

```
gcc tcg gtg gca ctg atc gcc tgc gac agt cgc ggc acg ccg tgg cag      1104
Ala Ser Val Ala Leu Ile Ala Cys Asp Ser Arg Gly Thr Pro Trp Gln
        355                 360                 365 agc acg cgc ggt ttt gcg ccg gag cgc gtg aac tgg ggc gaa ttg ctg      1152
Ser Thr Arg Gly Phe Ala Pro Glu Arg Val Asn Trp Gly Glu Leu Leu
    370                 375                 380 gac gac atg gcc gaa gtg cat atc cag tat gcg cag tcg atc gtg ccg      1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac      1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt      1296
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ttg cat      1344
Ala Ala Tyr Gln Leu Leu Asp Gly Leu Glu Gln Arg Leu Pro Leu His
        435                 440                 445 agc                                                                  1347
Ser

<210> SEQ ID NO 21
<211> LENGTH: 1347
<212> TYPE: DNA
<213> ORGANISM: Ralstonia solanacearum MAFF301526

<400> SEQUENCE: 21 atg agc aag aag att ctg tac gtc tat gcg ccg gcc ggc ccg ccg ctg       48
Met Ser Lys Lys Ile Leu Tyr Val Tyr Ala Pro Ala Gly Pro Pro Leu
1               5                   10                  15 gac tac tgt ttc ccg aaa atc gcc gcg cgc ggg gaa gtc cat acc tgc       96
Asp Tyr Cys Phe Pro Lys Ile Ala Ala Arg Gly Glu Val His Thr Cys
            20                  25                  30 atc gtc agc ccg ccg tcg gcc tcc aac atg gag atc ctg cgc cgg cac      144
Ile Val Ser Pro Pro Ser Ala Ser Asn Met Glu Ile Leu Arg Arg His
        35                  40                  45 agc cgt gcc gtg cat gac ttc agc cat gtc gcc ccg gcg cag gcg ctg      192
Ser Arg Ala Val His Asp Phe Ser His Val Ala Pro Ala Gln Ala Leu
    50                  55                  60 gag cag gtg cgc gcc ctg gcg cag cag atc ggc ccg gat gcg atc ttc      240
Glu Gln Val Arg Ala Leu Ala Gln Gln Ile Gly Pro Asp Ala Ile Phe
65                  70                  75                  80 aca ttc tcc gag ttc ctg ctg aaa tcg gtc tcg gaa ctg gcg gcc ggg      288
Thr Phe Ser Glu Phe Leu Leu Lys Ser Val Ser Glu Leu Ala Ala Gly
                85                  90                  95 ttc ggg ctg cgc gcg gtc ggc ccc aat atc gcg ctc ggg cgc aac aag      336
Phe Gly Leu Arg Ala Val Gly Pro Asn Ile Ala Leu Gly Arg Asn Lys
            100                 105                 110 gtg ctg atg cgc gaa cgc tgg cac cag gcc ggt atc ccg cag ccg gca      384
Val Leu Met Arg Glu Arg Trp His Gln Ala Gly Ile Pro Gln Pro Ala
        115                 120                 125 ttt cgc gcg gtc cgc agc gag cag gaa atc tcg cgc gtg gcc gag ctg      432
Phe Arg Ala Val Arg Ser Glu Gln Glu Ile Ser Arg Val Ala Glu Leu
    130                 135                 140 aac ttt ccg gtg ctg gtc aag ctg gcc tac ggc gcc ggc tcg atc ggc      480
Asn Phe Pro Val Leu Val Lys Leu Ala Tyr Gly Ala Gly Ser Ile Gly
145                 150                 155                 160 cag cag atc gtg aac ggc atg gac gag ttg ccg gcg gca atc gag cgc      528
Gln Gln Ile Val Asn Gly Met Asp Glu Leu Pro Ala Ala Ile Glu Arg
                165                 170                 175
```

```
ctg att gcc gcc acg gag gcg gca cgc agg gcg ggc aag cac gag ttt       576
Leu Ile Ala Ala Thr Glu Ala Ala Arg Arg Ala Gly Lys His Glu Phe
            180                 185                 190 tcc gaa cac gag ggc ttt ccg cag ctg atc gcc gaa gag atc att cag       624
Ser Glu His Glu Gly Phe Pro Gln Leu Ile Ala Glu Glu Ile Ile Gln
        195                 200                 205 tcc acc acc acc tcg tgg tac gac gaa gac ggc tac ggc gac tac ctg       672
Ser Thr Thr Thr Ser Trp Tyr Asp Glu Asp Gly Tyr Gly Asp Tyr Leu
    210                 215                 220 agc gtg gaa ggg ctg gtg cgc gac ggt gtg tac tac ccg ttg gcc atg       720
Ser Val Glu Gly Leu Val Arg Asp Gly Val Tyr Tyr Pro Leu Ala Met
225                 230                 235                 240 acc ggc cgg ctg cgc acc att gcg ccg ttt acc gaa ctc ggc aat gtg       768
Thr Gly Arg Leu Arg Thr Ile Ala Pro Phe Thr Glu Leu Gly Asn Val
                245                 250                 255 gcg ccg tgc gtg ctg agc acg gac aag aag gca aag atc gtt gcg ctg       816
Ala Pro Cys Val Leu Ser Thr Asp Lys Lys Ala Lys Ile Val Ala Leu
            260                 265                 270 atc aag cgg tcg atc gat gcg ctt ggc ttc gag aac tgc gcc acc cac       864
Ile Lys Arg Ser Ile Asp Ala Leu Gly Phe Glu Asn Cys Ala Thr His
        275                 280                 285 acc gag ctc aag ctg atg gcg gac ggc gag gtg tcg ttc ctg gag acc       912
Thr Glu Leu Lys Leu Met Ala Asp Gly Glu Val Ser Phe Leu Glu Thr
    290                 295                 300 gcc gcc cgc atg ggc ggc gtg gcg atc gcc aag gag ctg gac gaa gta       960
Ala Ala Arg Met Gly Gly Val Ala Ile Ala Lys Glu Leu Asp Glu Val
305                 310                 315                 320 ttc ggg atc gat tat gtc gac ctg ttt ctg agc gtg atc ctg ggc gag      1008
Phe Gly Ile Asp Tyr Val Asp Leu Phe Leu Ser Val Ile Leu Gly Glu
                325                 330                 335 ccg gag acg att ccg gca ttc gag cag aac gcg ccg cgc tgt gcc gcg      1056
Pro Glu Thr Ile Pro Ala Phe Glu Gln Asn Ala Pro Arg Cys Ala Ala
            340                 345                 350 gcc tcg gtg gca ctg atc gcc tgc gac agt cgc ggc acg ccg tgg cag      1104
Ala Ser Val Ala Leu Ile Ala Cys Asp Ser Arg Gly Thr Pro Trp Gln
        355                 360                 365 agc acg cgc ggt ttt gcg ccg gag cgc gtg aac tgg ggc gaa ttg ctg      1152
Ser Thr Arg Gly Phe Ala Pro Glu Arg Val Asn Trp Gly Glu Leu Leu
    370                 375                 380 gac gac atg gcc gaa gtg cat atc cag tat gcg cag tcg atc gtg ccg      1200
Asp Asp Met Ala Glu Val His Ile Gln Tyr Ala Gln Ser Ile Val Pro
385                 390                 395                 400 ggc agc ccg atc gct ccc tac gac att tcc gga ggg ttg atg aac tac      1248
Gly Ser Pro Ile Ala Pro Tyr Asp Ile Ser Gly Gly Leu Met Asn Tyr
                405                 410                 415 gcc ggc cag gca ttc ctg gta agc ccg acg ccg gcc gag ctc aag cgt      1296
Ala Gly Gln Ala Phe Leu Val Ser Pro Thr Pro Ala Glu Leu Lys Arg
            420                 425                 430 gct gcg tac cag ttg ctg gac ggc ctg gag cag cgt ttg ccg ctg cat      1344
Ala Ala Tyr Gln Leu Leu Asp Gly Leu Glu Gln Arg Leu Pro Leu His
        435                 440                 445 agc                                                                   1347
Ser

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued

```
      DNA

<400> SEQUENCE: 22
gggccaacca tatgagcaag aagattct                                         28

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
atatctcgag gctatgcagc ggcaaac                                          27
```